US012048739B2

(12) United States Patent
Burki et al.

(10) Patent No.: US 12,048,739 B2
(45) Date of Patent: Jul. 30, 2024

(54) PURIFIED CAPSULAR POLYSACCHARIDES OF *STREPTOCOCCUS PNEUMONIAE*

(71) Applicant: Biological E Limited, Telangana (IN)

(72) Inventors: Rajendar Burki, Telangana (IN); Vivek Babu Kandimalla, Telangana (IN); Rajan Sriraman, Telangana (IN); Ramesh Venkat Matur, Telangana (IN); Narender Dev Mantena, Telangana (IN); Mahima Datla, Telangana (IN); Veerapandu Sangareddy, Telangana (IN)

(73) Assignee: Biological E Limited (IN)

( * ) Notice: Subject to any disclaimer, the term of this patent is extended or adjusted under 35 U.S.C. 154(b) by 0 days.

(21) Appl. No.: 17/278,181

(22) PCT Filed: Sep. 23, 2019

(86) PCT No.: PCT/IB2019/058036
§ 371 (c)(1),
(2) Date: Mar. 19, 2021

(87) PCT Pub. No.: WO2020/058963
PCT Pub. Date: Mar. 26, 2020

(65) Prior Publication Data
US 2021/0346488 A1 Nov. 11, 2021

(30) Foreign Application Priority Data
Sep. 23, 2018 (IN) .............................. 201841031653
Sep. 23, 2018 (IN) .............................. 201841031654

(51) Int. Cl.
*A61K 39/02* (2006.01)
*A61K 31/715* (2006.01)
*A61K 39/09* (2006.01)
*A61K 47/62* (2017.01)
*C08B 37/00* (2006.01)
*A61K 39/00* (2006.01)

(52) U.S. Cl.
CPC .......... *A61K 39/092* (2013.01); *A61K 31/715* (2013.01); *A61K 47/62* (2017.08); *C08B 37/0003* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| 4,365,170 A | 12/1982 | Okuhara |
| 4,673,574 A | 6/1987 | Anderson |
| 5,614,382 A | 3/1997 | Metcalf |
| 9,492,559 B2 | 11/2016 | Emini et al. |
| 2016/0324949 A1* | 11/2016 | Han .................... A61K 39/385 |

FOREIGN PATENT DOCUMENTS

| WO | WO 93/15760 | 8/1993 |
| WO | WO 95/08348 | 3/1995 |
| WO | WO 96/29094 | 9/1996 |
| WO | WO 98/42721 | 10/1998 |
| WO | WO 2016/079755 | 5/2016 |
| WO | WO 2017/067962 | 4/2017 |
| WO | WO 2017/081700 | 5/2017 |
| WO | 2017/173415 A2 | 10/2017 |
| WO | WO 2018/193475 | 10/2018 |
| WO | WO 2019/050814 | 3/2019 |
| WO | WO 2019/050815 | 3/2019 |
| WO | WO 2019/050816 | 3/2019 |

OTHER PUBLICATIONS

Caroff et al (Can. J. Biochem. 1984. 62:151-161).*
https://en.wikipedia.org/wiki/Polysaccharide (see bacterial polysaccharide section) last edited Jun. 15, 2022.*
Lin et al (Immunology. 2010. 215: 545-550).*
Aljanaby, "Study the ability of using sesame oil as an adjuvant," Journal of Babylon University/Pure and Applied Sciences 21(5):1648-1656 (publication date: Aug. 2013).
Bethell et al., "A novel method of activation of cross-linked agaroses with 1,1'-carbonyldiimidazole which gives a matrix for affinity chromatography devoid of additional charged groups," J Biol Chem 254(8):2572-4 (publication date: Apr. 25, 1979).
Beynon et al., Characterization of the capsular antigen of *Streptococcus pneumoniae* serotype 35B1, Can. J. Chem. 73:41-48 (1995).
Chu et al., "Further Studies on the Immunogenicity of Haemophilus influenzae Type b and Pneumococcal Type 6A Polysaccharide-Protein Conjugates," Infect Immun.y 40(1):245-256 (publication date: Apr. 1983).
Hearn et al., "Application of 1,1'-carbonyldiimidazole-activated matrices for the purification of proteins. III. The use of 1,1'-carbonyldiimidazole-activated agaroses in the biospecific affinity chromatographic isolation of serum antibodies," J Chromatogr 218:509-18 (publication date: Nov. 20, 1981).
International Search Report and Written Opinion dated Aug. 1, 2021 for International Application No. PCT/IB2019/058036.
Ubukata et al., Serotype Changes and Drug Resistance in Invasive Pneumococcal Diseases in Adults after Vaccinations in Children, Japan, 2010-2013, Emerging Infectious Diseases 21(11):1956-1965 (publication date: Nov. 2015).
Venkateswaran et al., Type Variation of Strains of *Streptococcus pneumoniae* in Capsular Serogroup 15, the Journal of Infectious Diseases 147(6):1041-1054 (publication date: Jun. 1983).
Dagan et al., "Glycoconjugate vaccines and immune interference: A review," Vaccine 28:5513-5523 (publication date: Jun. 25, 2010).
Poolman et al., "The history of pneumococcal conjugate vaccine development: dose selection," Expert Reviews Vaccines 12(12):1379-1394 (2013).

* cited by examiner

*Primary Examiner* — Jennifer E Graser
(74) *Attorney, Agent, or Firm* — Perkins Coie LLP

(57) ABSTRACT

The invention relates to capsular polysaccharides of *Streptococcus pneumoniae*. More specifically, the present invention relates to sized and purified capsular polysaccharides of *Streptococcus pneumoniae* serotypes 2, 15A, 15C & 35B and process for their preparation.

12 Claims, 9 Drawing Sheets

A)

B)

(A)

(B)

(A)

(B)

(A)

(B)

(A)

(B)

PURIFIED CAPSULAR POLYSACCHARIDES OF *STREPTOCOCCUS PNEUMONIAE*

CROSS-REFERENCE TO RELATED APPLICATION(S)

This application is a 371 U.S. National Stage application of International PCT Application No. PCT/IB2019/058036, filed Sep. 23, 2019, which claims the benefit of priority to Indian Patent Application Nos. 201841031653 and 201841031654, filed on Sep. 23, 2018, which are hereby incorporated by reference herein in their entirety.

TECHNICAL FIELD

The present invention relates to purified capsular polysaccharides of *Streptococcus pneumoniae*. More specifically, the present invention relates to purified and sized capsular polysaccharides of *Streptococcus pneumoniae* serotypes 2, 15A, 15C & 35B and process for their preparation.

BACKGROUND

*Streptococcus pneumoniae* is a gram-positive bacterium which is a major causative agent in invasive infections in animals and humans, such as sepsis, meningitis, otitis media and lobar pneumonia. As part of the infective process, pneumococci readily bind to non-inflamed human epithelial cells of the upper and lower respiratory tract by binding to eukaryotic carbohydrates in a lectin-like manner.

Pneumococcus is encapsulated with a chemically linked polysaccharide which confers serotype specificity. There are more than 90 known serotypes of pneumococci, and the capsule is the principle virulence determinant for pneumococci, as the capsule not only protects the inner surface of the bacteria from complement but is itself poorly immunogenic. Anti-polysaccharide antibody level has been regarded as predictive for the protection against invasive pneumococcal disease. As a vaccine, the pneumococcal polysaccharide coat can confer a reasonable degree of immunity to *Streptococcus pneumoniae* in individuals with developed or unimpaired immune systems, but the capsular polysaccharide conjugated to a suitable carrier protein allows for an immune response in infants and elderly who are also at most risk for pneumococcal infections.

Pneumococcal vaccines include pneumococcal polysaccharide vaccine and pneumococcal conjugate vaccines. It is generally accepted that the protective efficacy of the commercialized pneumococcal polysaccharide vaccine is more or less related to the concentration of antibody-induced upon vaccination. Current vaccines include multivalent pneumococcal polysaccharide vaccines (comprises pneumococcal polysaccharides from two or more serotypes) and pneumococcal conjugate vaccines.

Pneumovax® 23 is a multivalent pneumococcal polysaccharide vaccine and contains unconjugated capsular polysaccharides from 23 pneumococcal serotypes including serotypes 1, 2, 3, 4, 5, 6B, 7F, 8, 9N, 9V, 10A, 11A, 12F, 14, 15B, 17F, 18C, 19F, 19A, 20, 22F, 23F and 33F. Pneumovax®23, that has been licensed proved valuable in preventing pneumococcal disease in adults, particularly, the elderly and those at high-risk. However, infants and young children respond poorly to these unconjugated pneumococcal polysaccharide vaccines.

Prevnar®7 is a pneumococcal polysaccharide-protein conjugate vaccine and includes the seven most frequently isolated polysaccharide serotypes (e.g., 4, 6B, 9V, 14, 18C, 19F, and 23F conjugated to $CRM_{197}$). Since the use of Prevnar®-7 began in the United States in 2000, there has been a significant reduction in invasive pneumococcal disease (IPD) in children. A 13-valent conjugate vaccine Prevenar-13®, containing thirteen serotypes 1, 3, 4, 5, 6A, 6B, 7F, 9V, 14, 18C, 19A, 19F and 23F conjugated to $CRM_{197}$, was developed and approved due to the limitations in serotype coverage with Prevnar®-7 in certain regions of the world.

Synflorix® is a pneumococcal conjugate vaccine that includes ten polysaccharide serotypes 1, 4, 5, 6B, 7F, 9V, 14, 23F—conjugated to protein D (PD), serotype 18C conjugated to tetanus toxoid (TT) and serotype 19F conjugated to diphtheria toxoid (DT). Each of the serotype polysaccharides is coupled utilizing 1-cyano-4-dimethylamino-pyridinium tetrafluoroborate (CDAP) under controlled pH.

U.S. Pat. No. 9,492,559B2 discloses an immunogenic composition comprising at least one glycoconjugate selected from the group consisting of a glycoconjugate from *Streptococcus pneumoniae* serotype 15B, a glycoconjugate from *Streptococcus pneumoniae* serotype 22F, a glycoconjugate from *Streptococcus pneumoniae* serotype 33F, a glycoconjugate from *Streptococcus pneumoniae* serotype 12F, a glycoconjugate from *Streptococcus pneumoniae* serotype 10A, a glycoconjugate from *Streptococcus pneumoniae* serotype 11A and a glycoconjugate from *Streptococcus pneumoniae* serotype 8. WO 2019/050813A1 discloses a purified capsular polysaccharide from *Streptococcus pneumoniae* serotype 16F, and polysaccharide protein conjugate thereof.

WO 2019/050814A1 discloses a purified capsular polysaccharide from *Streptococcus pneumoniae* serotypes 23A and 23B, and polysaccharide-protein conjugate thereof.

WO 2019/050815A1 discloses a purified capsular polysaccharide from *Streptococcus pneumoniae* serotype 24F, and polysaccharide-protein conjugate thereof.

WO 2019/050816A1 discloses a purified capsular polysaccharide from *Streptococcus pneumoniae* serotype 31, and polysaccharide-protein conjugate thereof.

Despite these vaccines, there is a need for the development of additional multivalent pneumococcal conjugate vaccines with polysaccharides which are purified and sized in a simple and efficient manner. Hence the inventors of the present invention have purified and sized capsular polysaccharides of *Streptococcus pneumoniae* serotypes 2, 15A, 15C & 35B in simple and efficient manner.

SUMMARY

The invention relates to a purified and sized capsular polysaccharide of *Streptococcus pneumoniae* serotype 2 having an average molecular weight between about 50 and 1000 kDa.

The invention also relates to a purified and sized capsular polysaccharide of *Streptococcus pneumoniae* serotype 15A having an average molecular weight between about 50 and 1000 kDa.

The invention also relates to a purified and sized capsular polysaccharide of *Streptococcus pneumoniae* serotype 15C having an average molecular weight between about 50 and 1000 kDa.

The invention also relates to a purified and sized capsular polysaccharide of *Streptococcus pneumoniae* serotype 35B having an average molecular weight between about 50 and 1000 kDa.

DEFINITIONS

Figure 1:
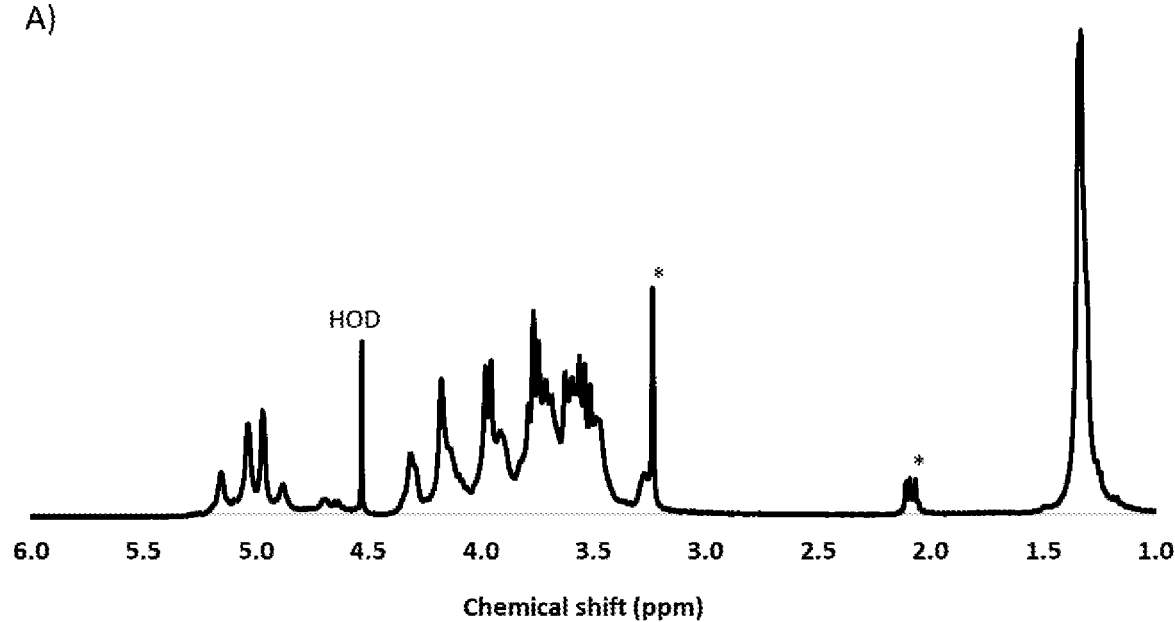
FIG. 1A: 400 MHz one dimensional (1D)$_1$H NMR spectrum of the capsular polysaccharide of Serotype 2 in D$_2$O at 50° C.
FIG. 1B: One dimensional (1D) $^1$H NMR identity region used for identification of serotype 2.
Figure 1:
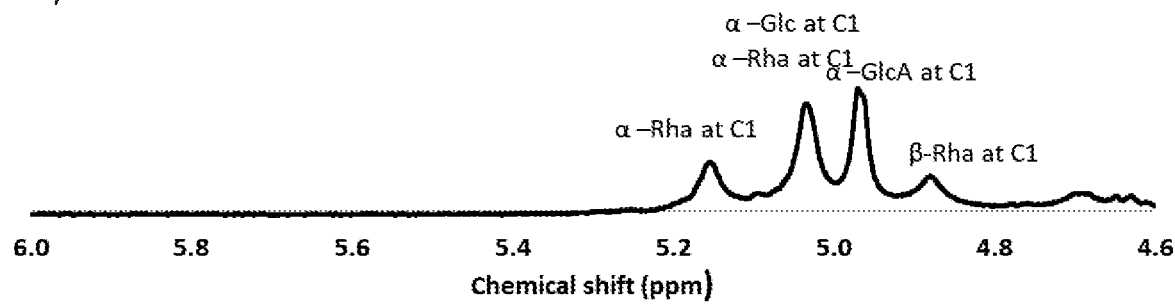

Throughout this invention, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this invention to mean including at least the recited feature(s) such that any greater number of the same feature(s) and/or one or more additional types of features are not precluded. Furthermore, various particular features, methods, or characteristics may be combined in any suitable manner in one or more embodiments.

This invention is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain embodiments of the present technology disclosed in the context of particular embodiments may be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology may encompass other embodiments not expressly shown and/or described herein.

Unless defined otherwise, all technical and scientific terms used herein have the same meaning as commonly understood by one of ordinary skill in the art to which the methods belong.

Where a range of values is provided, it is understood that each intervening value between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods, compositions and combinations.

As used herein, the term "capsular polysaccharide" refers to a layer of polysaccharide external to but contiguous with the cell wall of *Streptococcus pneumoniae* serotypes 2, 15A, 15C and 35B.

As used herein, the term "carrier protein" refers to any protein to which the polysaccharide is coupled or attached or conjugated, typically for the purpose of enhancing or facilitating detection of the antigen by the immune system. Examples of carrier proteins include, but are not limited to CRM$_{197}$, PsaA and Tetanus toxoid.

The term "conjugate" or "conjugated" as used herein is used to mean that a *Streptococcus pneumoniae* capsular polysaccharide is covalently bonded to a carrier protein.

The term "polysaccharide" as used in this specification refers to a complex carbohydrate composed of saccharide chains joined together by glycosidic bonds. The polysaccharide may contain at least 10, 20, 30, 40 or 50 or more saccharides.

The term "sized" or "sizing" as used herein refers to reducing the size of a native polysaccharide by various methods. The methods may include mechanical methods, such as homogenization. Reducing the size of a native polysaccharide or "sizing" provides various advantages which include: (1) imparting more homogenous as compared to the native polysaccharides (2) the ratio of polysaccharide to protein in the conjugate can be controlled (3) sized polysaccharides may provide greater stability to the composition. For the purposes of this invention, native capsular polysaccharides of *Streptococcus pneumoniae* serotype 2, 15A, 15C and 35B have been sized to an average molecular weight (Mw) between 50 and 1000 kDa.

The term "Molecular weight" or "Molecular size" or "Average Molecular size" or "Average molecular weight" of a polysaccharide as used herein refers to the weight-average molecular weight (Mw) of the polysaccharide measured by MALLS (Multi-Angle Laser Light Scattering).

DETAILED DESCRIPTION

The present invention relates to purified and sized capsular polysaccharides of *Streptococcus pneumoniae* serotypes 2, 15A, 15C and 35B and process for their preparation.

The polysaccharides according to the present invention are prepared by cultivating *Streptococcus pneumoniae* in an optimized nutrient within a fermenter and lysing the cells at the end of the fermentation by addition of sodium deoxycholate (DOC) or any conventional lysing agent. The harvested lysate broth is subjected to downstream purification to remove impurities like protein, nucleic acids, cell wall components, etc.

After fermentation, the DOC cell lysate is centrifuged on a batch or continuous centrifuge and the cell debris is removed. The pH of the cell-free broth adjusted to acidic condition and the temperature is increased, followed by centrifugation. Post centrifugation, the supernatant is passed through depth filter, concentrated and diafiltered using Ultra Filter (UF) membrane. Additional impurities are removed from polysaccharide preparation (retentate) by adding detergent(s) and followed by centrifugation. Subsequently, the detergent treated supernatant is passed through charcoal filter or activated carbon column, followed by exposing the filtered polysaccharide to $SiO_2$ particles and centrifugation. The supernatant is passed through depth filter and passing the depth filtrate through carbon filter followed by 0.22 to 0.6 μm filter. The filtrate is concentrated and diafiltered on UF membrane and diafiltered with 0.5 to 2% NaCl solution or in water or buffer to obtain polysaccharides obtained in substantially pure form.

The purified polysaccharide is sized either by chemically at high pH or mechanically using high-pressure homogenizer. Sized polysaccharide preparation is concentrated to 5 to 25 mg/mL on UF membrane. The retentate is passed through 0.22 μm filter and frozen below −20° C.

In one embodiment, the invention provides purified and sized capsular polysaccharides of *Streptococcus pneumoniae* serotypes 2, 15A, 15C and 35B having an average molecular weight (Mw) between 50 and 1000 kDa. Preferably, between 100-1000 kDa, 200-800 kDa, 250-600 kDa, or 300-400 kDa, 70-150 kDa, or 75-125 kDa.

In some embodiments, the purified capsular polysaccharides of *Streptococcus pneumoniae* serotype 2, 15A, 15C and 35B before conjugation have an average molecular weight of between 50 kDa and 1,000 kDa. In other such embodiments, the polysaccharide has an average molecular weight of between 50 kDa and 750 kDa; between 50 kDa and 500 kDa; between 100 kDa and 1,000 kDa; between 100 kDa and 750 kDa; between 100 kDa and 500 kDa.

The size of capsular polysaccharides of the present invention is reduced after the purification procedures using various sizing techniques to a desired size. The inventors have found that purified capsular polysaccharides from serotypes 2, 15A, 15C and 35B conjugated with carrier protein prepared according to the present invention has high immunogenicity.

In an embodiment, the capsular polysaccharides of the invention comprise *Streptococcus pneumoniae* polysaccharide from serotype 2 having an average molecular weight of about 80 kDa, 100 kDa, 200 kDa, 300 kDa, 400 kDa, 500 kDa, 700 kDa or 1000 kDa.

In an embodiment, the capsular polysaccharides of the invention comprise *Streptococcus pneumoniae* polysaccharide from serotype 15A having an average molecular weight of about 80 kDa, 100 kDa, 200 kDa, 300 kDa, 400 kDa, 500 kDa, 700 kDa or 1000 kDa.

In an embodiment, the capsular polysaccharides of the invention comprise *Streptococcus pneumoniae* polysaccharide from serotype 15C having an average molecular weight of about 80 kDa, 100 kDa, 200 kDa, 300 kDa, 400 kDa, 500 kDa, 700 kDa or 1000 kDa.

In an embodiment, the capsular polysaccharides of the invention comprise *Streptococcus pneumoniae* polysaccharide from serotype 35B having an average molecular weight of about 80 kDa, 100 kDa, 200 kDa, 300 kDa, 400 kDa, 500 kDa, 700 kDa or 1000 kDa.

In a further aspect, the present disclosure provides a sized *Streptococcus pneumoniae* serotype 15A capsular polysaccharide comprising glycerol content within a range of 5-18%, preferably 5 to 10%.

In a further aspect, the present disclosure provides a sized *Streptococcus pneumoniae* serotype 15C capsular polysaccharide comprising glycerol content within a range of 5-18%, preferably 5 to 10%.

In a further aspect, the present disclosure provides a sized *Streptococcus pneumoniae* serotype 35B capsular polysaccharide comprising acetate content within a range of 2-10%, preferably 2 to 8%.

In a further aspect, the present disclosure provides a sized *Streptococcus pneumoniae* serotype 15A having an average molecular weight between 50 to 1000 kDa and glycerol content within a range of 5-18%.

In a further aspect, the present disclosure provides a sized *Streptococcus pneumoniae* serotype 15C having an average molecular weight between 50 to 1000 kDa and glycerol content within a range of 5-18%.

In a further aspect, the present disclosure provides an isolated *Streptococcus pneumoniae* serotype 35B having an average molecular weight between 50 to 1000 kDa and acetate content within a range of 2-10%.

The presence of glycerol phosphate side chains can be determined by measurement of glycerol using high-performance anion-exchange chromatography with pulsed amperometric detection (HPAEC-PAD) after its release by treatment of the polysaccharide with hydrofluoric acid (HF).

In an embodiment, the present invention provides a pneumococcal conjugate vaccine, wherein purified polysaccharide from *Streptococcus pneumoniae* serotype 2 having an average molecular weight between 50 and 1000 kDa conjugated to a carrier protein selected from PsaA, CRM197, PspA or tetanus toxoid (TT), wherein the composition comprises a (w/w) percent ratio of protein to polysaccharide (protein/PS) of about 0.5 to about 2.0, preferably, 0.7 to 1.2.

In an embodiment, the present invention provides a pneumococcal conjugate vaccine, wherein the purified polysaccharide from *Streptococcus pneumoniae* serotype 15A having an average molecular weight between 50 and 1000 kDa conjugated to a carrier protein selected from PsaA, $CRM_{197}$, PspA or tetanus toxoid (TT), wherein the composition comprises a (w/w) percent ratio of protein to polysaccharide (protein/PS) of about 0.5 to about 2.0, preferably, 0.7 to 1.2.

In an embodiment, the present invention provides a pneumococcal conjugate vaccine, wherein purified polysaccharide from *Streptococcus pneumoniae* serotype 15C having an average molecular weight between 50 and 1000 kDa conjugated to a carrier protein selected from PsaA, CRM197, PspA or tetanus toxoid (TT), wherein the composition comprises having a (w/w) percent ratio of protein to polysaccharide (protein/PS) of about 0.5 to about 2.0 protein/PS, preferably, 0.7 to 1.2.

In an embodiment, the present invention provides a pneumococcal conjugate vaccine, wherein purified polysaccharide from Streptococcus pneumoniae serotype 35B having an average molecular weight between 50 and 1000 kDa conjugated to a carrier protein selected from PsaA, CRM197, PspA or tetanus toxoid (TT), wherein the composition comprises having a (w/w) percent ratio of protein to polysaccharide (protein/PS) of about 0.5 to about 2.0 protein/PS, preferably, 0.7 to 1.2.

In an embodiment, the present invention provides an immunogenic composition comprising at least one glycoconjugate from Streptococcus pneumoniae serotype 2, at least one glycoconjugate from Streptococcus pneumoniae serotype 15A, at least one glycoconjugate from Streptococcus pneumoniae serotype 15C and at least one glycoconjugate from 35B.

In one aspect, the immunogenic composition of the present invention further comprises glycoconjugates from Streptococcus pneumoniae serotypes 1, 3, 4, 5, 6A, 6B, 7F, 8, 9V, 10A, 11A, 14, 15B, 16F, 18C, 19A, 19F, 22F, 23A, 23B, 23F, 24F, 31, 33F, conjugated to carrier protein selected from PsaA, CRM197, PspA, tetanus toxoid (TT) or combination of CRM197 and PsaA or combination of CRM197 and Tetanus toxoid or combination of PsaA and Tetanus toxoid or combination of CRM197, PsaA and Tetanus toxoid.

In another aspect, the immunogenic composition is an 8, 9, 10, 11, 12, 13, 14, 15, 16, 17, 18, 19, 20, 22, 24, 25 or more valent pneumococcal conjugate composition.

In another aspect, the immunogenic composition is multivalent and comprises eight pneumococcal polysaccharide conjugates (eight valent), nine pneumococcal polysaccharide conjugates (9 valent), ten pneumococcal polysaccharide conjugates (10 valent), eleven pneumococcal polysaccharide conjugates (11 valent), twelve pneumococcal polysaccharide conjugates (12 valent), thirteen pneumococcal polysaccharide conjugates (13 valent), fourteen pneumococcal polysaccharide conjugates (14 valent), fifteen pneumococcal polysaccharide conjugates (15 valent), sixteen pneumococcal polysaccharide conjugates (16 valent), seventeen pneumococcal polysaccharide conjugates (17 valent), eighteen pneumococcal polysaccharide conjugates (18 valent), nineteen pneumococcal polysaccharide conjugates (19 valent), twenty pneumococcal polysaccharide conjugates (20 valent), twenty-one pneumococcal polysaccharide conjugates (21 valent), twenty-two pneumococcal polysaccharide conjugates (22 valent), twenty-three pneumococcal polysaccharide conjugates (23 valent), twenty-four pneumococcal polysaccharide conjugates (24 valent), twenty-five pneumococcal polysaccharide conjugates (25 valent), twenty-six pneumococcal polysaccharide conjugates (26 valent).

In yet another embodiment, the present invention provides an immunogenic composition comprising purified capsular polysaccharides of Streptococcus pneumoniae serotypes 2, 15A, 15C and 35B having an average molecular weight between about 50 and 1000 kDa conjugated to a carrier protein.

In one aspect of the invention, the immunogenic composition comprises Streptococcus pneumoniae polysaccharides wherein the polysaccharide serotypes are sized by a factor up to x2, x3, x4, x5, x6, x7, x8, x9 or x10. The term "sized by a factor up to x2" means that the saccharide is subjected to a process intended to reduce the size of the saccharide but to retain a size more than half the size of the native polysaccharide.

The polysaccharides which are not subjected to the process of sizing technique is referred to as native polysaccharide. A polysaccharide may become slightly reduced in size during normal purification procedures or by degradation during conjugation, which may still be referred as native polysaccharide.

The capsular polysaccharides may be size reduced by various mechanical means known in the art such as high pressure techniques such as microfluidization, Emulsiflex™, high pressure homogenization, sonication or Gaulin homogenization.

High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

In other embodiment, the present invention provides a pneumococcal polysaccharide-protein conjugate vaccine composition comprising capsular polysaccharide from Streptococcus pneumoniae serotype 2 conjugated to carrier protein, wherein polysaccharide-protein conjugate has an average molecular weight ranging between 500 kDa to about 10000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising capsular polysaccharide from Streptococcus pneumoniae serotype 15A conjugated to carrier protein, wherein polysaccharide-protein conjugate has an average molecular weight ranging between 500 kDa to about 10000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising capsular polysaccharide from Streptococcus pneumoniae serotype 15C conjugated to carrier protein, wherein polysaccharide-protein conjugate has an average molecular weight ranging between 500 kDa to about 10000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising capsular polysaccharide from Streptococcus pneumoniae serotype 35B conjugated to carrier protein, wherein polysaccharide-protein conjugate has an average molecular weight ranging between 500 kDa to about 10000 kDa and has a (w/w) percent ratio of protein to polysaccharide (protein/PS) of about 0.5 to about 2.0, preferably, 0.7 to 1.2.

The polysaccharide protein conjugate of the present invention has an average molecular weight ranging between 500 kDa to about 5000 kDa; 1,000 kDa to about 10,000 kDa; about 1,500 kDa to about 15,000 kDa; about 2,000 kDa to about 20,000 kDa; about 2,500 kDa to about 25,000 kDa; or about 3,000 kDa to about 30,000 kDa.

In another embodiment, the present invention provides a pneumococcal conjugate vaccine composition comprising purified pneumococcal polysaccharides and carrier proteins, having a percent ratio of protein to polysaccharide (protein/PS) of about 0.5 to about 2.0, preferably, 0.7 to 1.2.

In a preferred embodiment, the present invention provides a pneumococcal conjugate vaccine composition comprising purified polysaccharide from Streptococcus pneumoniae serotypes 2, 15A, 15C and 35B having an average molecular weight between 50 and 1000 kDa conjugated to a carrier protein selected from PsaA, CRM197, PspA, tetanus toxoid (TT), or combination of CRM197 and PsaA or combination of CRM197 and Tetanus toxoid or combination of PsaA and Tetanus toxoid or combination of CRM197, PsaA and Tetanus toxoid wherein the composition comprises a percent ratio of protein to polysaccharide (protein/PS) of about 0.5 to about 2.0, preferably, 0.7 to 1.2.

In another embodiment, the present invention provides a pneumococcal conjugate vaccine composition comprising one or more purified capsular pneumococcal polysaccharide serotype each individually conjugated to a carrier protein, wherein each polysaccharide-protein conjugate has an average molecular weight of about 1,500 kDa to about 15,000 kDa.

In other embodiments, the purified pneumococcal polysaccharides may be activated (e.g., chemically) prior to conjugation to one or more carrier proteins. Each activated pneumococcal polysaccharide may be each individually conjugated to a carrier protein forming a polysaccharide-protein conjugate (e.g., a glycoconjugate).

In some embodiments, the purified pneumococcal polysaccharides of the present invention may be chemically activated and subsequently conjugated to carrier proteins according to known techniques, such as those described in U.S. Pat. Nos. 4,365,170, 4,673,574 and 4,902,506. For example, pneumococcal polysaccharides can be activated by oxidation of a terminal hydroxyl group to an aldehyde with an oxidizing agent, such as periodate (e.g., sodium periodate, potassium periodate, or periodic acid) by random oxidative cleavage of one or more vicinal hydroxyl groups of the carbohydrates and formation of one or more reactive aldehyde groups.

The purified pneumococcal polysaccharides of the present invention may also be activated by CDAP (1-cyano-4-dimethylamino-pyridinium tetrafluoroborate) and subsequently conjugated to one or more carrier proteins such as PsaA, CRM197, PspA, or combination thereof. In other embodiments, pneumococcal polysaccharides activated with CDAP to form a cyanate ester may be directly conjugated to one or more carrier proteins or conjugated using a spacer (e.g., linker). The spacer may couple to an amino group on the carrier protein. In some embodiments, the spacer may be cystamine or cysteamine, which generates a thiolated polysaccharide that may be coupled to the carrier protein through a thioether linkage to a maleimide-activated carrier protein (e.g., using GMBS) or a haloacetylated carrier protein (e.g., using iodoacetimide, ethyl iodoacetimide HCl, STAB, SIA, SBAP, and/or N-succinimidyl bromoacetate. In other embodiments, the cyanate ester is coupled using hexane diamine or adipic acid dihydrazide (ADH) and an amino-derivatized saccharide is conjugated to a carrier protein using carbodiimide (e.g., EDAC or EDC) chemistry via a carboxyl group on the protein carrier. Such conjugates are described in PCT Publication No. WO 93/15760, PCT Publication No. WO 95/08348, PCT Publication No. WO 96/29094, and Chu et al., 1983, Infect. Immunity 40:245-256.

Other suitable activations and/or coupling techniques for use with the polysaccharide-protein conjugates and vaccine compositions of the present invention include use of carbodiimides, hydrazides, active esters, norborane, p-nitrobenzoic acid, N-hydroxysuccinimide, S—NHS, EDC, TSTU, and other methods described in PCT Publication No. WO 98/42721. For example, conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by coupling with a protein to form a carbamate linkage. In some embodiments, the anomeric terminus may be reduced to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

For example, another suitable activation and/or coupling techniques for use with the polysaccharide-protein conjugates and vaccine compositions of the present invention include the following method: sized pneumococcal polysaccharides (e.g., about 6 mL of sized polysaccharide at a concentration of about 10 mg/mL) and CDAP (e.g., about 100 mg/mL in acetonitrile (w/v)) can be mixed in a glass vial in a ratio of about 1 to about 1 (e.g., by stirring for about 1 minute). The pH of the polysaccharide solution may be adjusted as necessary (e.g., to about 9.25 with about 0.2M triethylamine and stirred for 3 min at room temperature). In addition, PsaA (e.g., about 4 mL of a solution having a concentration of about 15 mg/mL) may be added slowly to the activated pneumococcal polysaccharides (e.g., in a ratio of about 1 to about 1 (Ps: Carrier protein)). The pH of the reaction may be adjusted (e.g., to about 9.05 using 0.2M trimethylamine) and the reaction may be continued (e.g., by stirring for 5 hours at room temperature). The reaction mixture may be quenched (e.g., by addition of an excess concentration of glycine).

In some embodiments, the reaction mixture may be diafiltered using a membrane (e.g., a 100 K MWCO membrane) and may be purified by size-exclusion chromatography. The diafiltered and purified fractions may be analyzed using SEC-MALLS, and an anthrone method. The analyzed fractions containing conjugates may be pooled and sterile filtered (e.g., using 0.2 μm filters).

Following conjugation of pneumococcal polysaccharides to one or more carrier proteins, the polysaccharide-protein conjugates may be purified (e.g., enriched with respect to the amount of polysaccharide-protein conjugate) by a variety of techniques. These techniques include, but are not limited to concentration/diafiltration operations, precipitation/elution, column chromatography, and depth filtration. For example, after the conjugates are purified, the conjugates may be compounded to formulate the pneumococcal polysaccharide-protein conjugate compositions of the present invention, which may be used as vaccines.

In one embodiment, the present invention provides a 17 valent pneumococcal conjugate vaccine composition comprising polysaccharides from serotype of *Streptococcus pneumoniae* conjugated to a carrier protein, wherein the serotypes comprise 2, 15A, 15C & 35 B and additional serotypes 1, 3, 4, 5, 6A, 6B, 7F, 9V, 14, 18C, 19A, 19F, 23F.

In one embodiment, the present invention provides a 17 valent pneumococcal conjugate vaccine composition comprising polysaccharides from serotype of *Streptococcus pneumoniae* conjugated to a carrier protein, wherein the serotypes comprise 2, 15A, 15C & 35B and additional serotypes 1, 3, 4, 5, 6A, 6B, 7F, 9V, 14, 18C, 19A, 19F, 23F, wherein the carrier protein is selected from PsaA, CRM197, PspA, tetanus toxoid (TT).

In one embodiment, the present invention provides a 24 valent pneumococcal conjugate vaccine composition comprising polysaccharides from at least 3 pneumococcal serotype selected from 2, 15A, 15C & 35B and additional serotypes comprising of 1, 3, 4, 5, 6A, 6B, 7F, 8, 9V, 10A, 11A, 14, 18C, 19A, 19F, 20A, 20B, 22F, 23F, 24F, 33F wherein the 24 serotypes are conjugated to a carrier protein, wherein the carrier protein is selected from PsaA, CRM197, PspA, tetanus toxoid (TT) or combination of CRM197 and PsaA or combination of CRM197 and Tetanus toxoid or combination of PsaA and Tetanus toxoid or combination of CRM197, PsaA and Tetanus toxoid.

In one embodiment, the present invention provides a 24 valent pneumococcal conjugate vaccine composition comprising polysaccharides from at least 2 pneumococcal serotype selected from 2, 15A, 15C & 35B and additional serotypes comprising of 1, 3, 4, 5, 6A, 6B, 7F, 8, 9V, 10A, 11A, 12F, 14, 18C, 19A, 19F, 22F, 23A, 23B, 23F, 24F, 33F wherein the 24 serotypes are conjugated to a carrier protein selected from PsaA, CRM197, PspA, tetanus toxoid (TT) or combination of CRM197 and PsaA or combination of CRM197 and Tetanus toxoid or combination of PsaA and Tetanus toxoid or combination of CRM197, PsaA and Tetanus toxoid.

In one embodiment, the present invention provides a multivalent pneumococcal conjugate vaccine composition comprising polysaccharides from at least 2 pneumococcal serotype selected from 2, 15A, 15C & 35B and one or more additional serotypes selected from 1, 3, 4, 5, 6A, 6B, 7F, 8, 9V, 10A, 11A, 12F, 14, 18C, 19A, 19F, 20A, 20B, 22F, 23A, 23B, 23F, 24F, 33F wherein the serotypes are conjugated to a carrier protein, selected from PsaA, CRM197, PspA, tetanus toxoid (TT) or combination of CRM197 and PsaA or combination of CRM197 and Tetanus toxoid or combination of PsaA and Tetanus toxoid or combination of CRM197, PsaA and Tetanus toxoid.

In some embodiments, the present invention provides a method for preparing a polysaccharide-protein conjugate of the pneumococcal vaccine composition described herein wherein the method further comprises formulating the polysaccharide-protein conjugate into the pneumococcal vaccine composition including an adjuvant, an excipient, and a buffer.

In some embodiments, the present invention provides a method for preparing a polysaccharide-protein conjugate of the pneumococcal vaccine composition described herein wherein the adjuvant is aluminium phosphate.

In another embodiment, the vaccine or immunogenic composition of this invention is used for prophylaxis against an infection caused by Streptococcus pneumoniae strains.

In some embodiments, the present invention provides a method of treating a subject in need thereof comprising, administering a pneumococcal vaccine composition described herein to the subject in need thereof.

In some embodiments, the subject has a disease mediated by Streptococcus pneumoniae, such as invasive pneumococcal disease (IPD). In one embodiment, the subject is a human, such as an infant (less than about 1 year of age), a toddler (about 12 months to about 24 months of age), a young child (about 2 years to about 5 years of age), an older child (about 5 years to about 13 years of age), an adolescent (about 13 years to about 18 years of age), an adult (about 18 years to about 65 years of age), or an elder (more than about 65 years of age).

In some embodiments, the present invention provides a method of inducing an immune response to a Streptococcus pneumoniae capsular polysaccharide conjugate comprising administering an immunologically effective amount of the pneumococcal conjugate vaccine composition described herein to a subject.

In one embodiment, method of inducing an immune response to a Streptococcus pneumoniae capsular polysaccharide conjugate, comprising administering the pneumococcal conjugate vaccine composition described herein to the subject systemically, subcutaneously, and/or mucousally.

In some embodiments, an amount of each conjugate in a dose of the vaccine compositions of the present invention is an amount sufficient to induce an immunoprotective response, such as an immunoprotective response without significant, adverse effects. While the amount of each conjugate may vary depending upon the pneumococcal serotype, each dose of the vaccine compositions may comprise about 0.1 µg to about 50 µg of each pneumococcal polysaccharide, about 0.1 µg to about 10 µg, or about 1 µg to about 5 µg of each pneumococcal polysaccharide conjugated to each carrier protein comprising about 1.5 µg to about 5 µg of carrier protein.

In other embodiment, the present invention provides a pneumococcal polysaccharide-protein conjugate vaccine composition comprising 0.1 µg to about 10 µg of capsular polysaccharide from Streptococcus pneumoniae serotype 2 conjugated to 1.5 µg to about 5 µg of carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.1 µg to about 10 µg of capsular polysaccharide from Streptococcus pneumoniae serotype 15A conjugated to 1.5 µg to about 5 µg of carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.1 µg to about 10 µg of capsular polysaccharide from Streptococcus pneumoniae serotype 15C conjugated to 1.5 µg to about 5 µg of carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.1 µg to about 10 µg of capsular polysaccharide from Streptococcus pneumoniae serotype 35B conjugated to 1.5 µg to about 5 µg of carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from Streptococcus pneumoniae serotype 2 conjugated to 1.5 µg to about 5 µg of $CRM_{197}$ carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from Streptococcus pneumoniae serotype 15A conjugated to 1.5 µg to about 5 µg of $CRM_{197}$ carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from *Streptococcus pneumoniae* serotype 15C conjugated to 1.5 µg to about 5 µg of CRM197 carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from *Streptococcus pneumoniae* serotype 2 conjugated to 1.5 µg to about 5 µg of PsaA carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from *Streptococcus pneumoniae* serotype 15A conjugated to 1.5 µg to about 5 µg of PsaA carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from *Streptococcus pneumoniae* serotype 15C conjugated to 1.5 µg to about 5 µg of PsaA carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In other embodiment, the present invention provides a pneumococcal polysaccharide-protein conjugate vaccine composition comprising 0.5 µg to about 5 µg of capsular polysaccharide from *Streptococcus pneumoniae* serotype 35B conjugated to 1.5 µg to about 5 µg of PsaA carrier protein, wherein polysaccharide-protein conjugate has an average molecular weight ranging between 500 kDa to about 15000 kDa and has a (w/w) percent ratio of protein to polysaccharide (protein/PS) of about 0.5 to about 2.0, preferably, 0.7 to 1.2.

In a preferred embodiment, the present invention provides a multivalent conjugate vaccine composition comprising at least two polysaccharides from *Streptococcus pneumoniae* serotypes 2, 15A, 15C and 35B having an average molecular weight between 50 and 1000 kDa conjugated to a carrier protein selected from PsaA, $CRM_{197}$, PspA, tetanus toxoid (TT), wherein the composition comprises a percent ratio of protein to polysaccharide (protein/PS) of about 0.5 to about 2.0, preferably, 0.7 to 1.2 and additional polysaccharide protein conjugate from *Streptococcus pneumoniae* serotypes 1, 3, 4, 5, 6A, 6B, 7F, 8, 9V, 10A, 11A, 14, 16F, 18C, 19A, 19F, 22F, 23A, 23B, 23F, 24F, 31, 33F, conjugated to a carrier protein selected from PsaA, CRM197, PspA, tetanus toxoid (TT) or combination of carrier proteins.

The pneumococcal polysaccharide-protein conjugate vaccine compositions of the present invention may be manufactured using known methods. For example, the pneumococcal polysaccharide-protein conjugate vaccine compositions may be formulated with a pharmaceutically acceptable diluent or vehicle, e.g., water or a saline solution. In addition, the pneumococcal polysaccharide-protein conjugate vaccine compositions may further include one or more of the following: a buffer, a preservative or a stabilizer, polysorbate, an adjuvant such as an aluminum compound, e.g., an aluminium hydroxide, an aluminium phosphate or an aluminium hydroxyphosphate, and/or a lyophilization excipient. Inclusion of any one of the above compounds in the pneumococcal polysaccharide-protein conjugate vaccine compositions of the present invention may be selected as a function of the mode and route of administration to a subject in need thereof and may further be based on standard pharmaceutical practices.

The pneumococcal polysaccharide-protein conjugate vaccine compositions of the present invention, when administered to a subject, induces the formation of antibodies capable of binding to serotypes 2, 15A, 15C and 35B of *Streptococcus pneumoniae* as measured by a standard ELISA assay. The ELISA was performed as per the WHO suggested protocol. Briefly, Maxisorp™ ELISA plates were coated with PnCPS of given serotype (1 µg/50 µL/well using PBS; sterile endotoxin free, with 0.02% sodium azide). Plates were placed in a box with moistened paper towels for humidification and incubated at 37° C.±2° C. for 5 hrs, the plates were then stored at 5° C.±3° C. until use.

EXAMPLES

The following examples are provided to illustrate the invention and are merely for illustrative purpose only and should not be construed to limit the scope of the invention.

Example 1 a. Preparation of Pneumococcal Capsular Polysaccharide Serotypes 2, 15A, 15C and 35B The cell banks of *Streptococcus pneumoniae* strains (for serotypes 2, 15A, 15C and 35B) was obtained from Centre for Disease Control and Prevention, USA.

Pre-Seed Preparation:

0.4 µl of culture (*Streptococcus pneumonia* serotype 2) isolate was inoculated into 60 ml of complete Mueller Hinton (MH) media. The inoculated flask was incubated for 2 to 8 hours at 35±1° C., 5±0.5% $CO_2$. Samples were collected and checked for optical density at 600 nm. Once the desired OD reaches to 0.8±0.2 samples were collected and checked for pH and gram staining.

Seed Preparation:

Post confirming the purity by microscopy (Gram staining) of pre-seed culture, 40 ml of pre-seed culture was inoculated into one litre flask containing 760 mL of MH media. The inoculated seed was incubated for 3 to 11 hours at 35±1° C., 5±0.5% % $CO_2$. Samples were collected and checked for optical density (OD) at 600 nm. Once the desired OD reaches to 4±2 sample were collected for gram staining, pH. Purity was confirmed by plating on Blood agar plate.

Fermentation/Culturing:

750 ml of the seed was inoculated into 15 litres of MH Medium and 30 to 50% of glucose was supplemented at the rate of 3 to 5 ml per minute until the OD at 600 nm reaches 6±2 at 35±1° C. under 100 to 140 revolution per minute (RPM) at a pH of 7.1±0.3.

Inactivation:

13% stock solution of sodium deoxycholate (DOC) was added to the fermenter broth for inactivation of the culture broth and incubated for 10±2 hrs.

Centrifugation:

DOC treated culture was harvested and centrifuged at 14000 relative centrifugal force (RCF) at 20° C. After centrifugation, the supernatant was collected and processed for purification steps.

b. Purification of Pneumococcal Capsular Polysaccharides Serotype 2

*Streptococcus pneumoniae* serotype 2 DOC cell lysate was centrifuged on batch centrifuge and the cell debris was removed. Then the pH of the cell free broth was adjusted to 5.0, and incubated for 4 hours and centrifuged for 45 minutes at 14000 g. Post centrifugation, the supernatant was passed through depth filter. Then, the filtrate was concentrated to 4.2× and diafiltered (4-15 Dia volumes) using 30-300 kDa UF membrane. Additional impurities were removed from polysaccharide preparation (retentate) by adding detergent (CTAB 1%) and incubated for 30 to 90 minutes, at 6° C. followed by centrifugation for 15-60 minutes at 9000 to 14500 g. Subsequently, the CTAB treated supernatant was passed through an activated carbon column (30-300 g/L poly preparation). Carbon filtrated polysaccharide preparation was exposed to $SiO_2$ (Silicon Dioxide) particles (3-10%, with salt) and incubated for 15-120 minutes at 2 to 40° C. followed by, centrifugation for 15-60 min at 9000 to 14500 g. The supernatant was passed through 2 to 50 μm depth filter and the depth filtrate was passed though carbon filter followed by 0.22 to 0.6 μm filter. Then, the filtrate (0.22 to 0.6 μm) was concentrated and diafiltered on 30-300 kDa UF membrane and diafiltered with 0.5 to 2% NaCl solution or without salt in water or buffer to obtain capsular polysaccharide serotype 2 in substantially pure form.

Purification of Pneumococcal Capsular Polysaccharides from Serotypes 15A and 15C were Prepared in a Similar Procedure Described Above for Serotype 2.

c. Purification of Pneumococcal Capsular Polysaccharides Serotype 35B

*Streptococcus pneumoniae* serotype 35B, DOC cell lysate was centrifuged on batch centrifuge and the cell debris was removed. Then pH of the cell free broth was adjusted to 5.0, and incubated for 4 hours and centrifuged for 45 minutes at 14000 g. Post centrifugation, the supernatant was passed through depth filter. Then, the filtrate was concentrated to 7.5× and diafiltered (4-15 Dia volumes) using 30-300 kDa UF membrane. Additional impurities were removed from polysaccharide preparation (retentate) by adding detergent (CTAB 1%) and incubated for 30 to 90 minutes, at 6° C. followed by centrifugation for 15-60 minutes at 9000 to 14500 g. Subsequently, the CTAB treated supernatant was passed through an activated carbon column (30-300 g/L poly preparation). Carbon filtrated polysaccharide preparation was exposed to $SiO_2$ (Silicon Dioxide) particles (3-10%, with salt) and incubated for 15-120 minutes at 2 to 40° C. followed by, centrifugation for 15-60 min at 9000 to 14500 g. Supernatant was passed through 2 to 50 μm depth filter and the depth filtrate was passed through carbon filter followed by 0.22 to 0.6 μm filter. Then, the filtrate (0.22 to 0.6 μm) was concentrated and diafiltered on 30-300 kDa UF membrane and diafiltered with 0.5 to 2% NaCl solution or without salt in water or buffer to obtain capsular polysaccharide serotype 35B in substantially pure form.

d. Sizing of the Purified Pneumococcal Capsular Polysaccharide Serotype 2

Purified pneumococcal capsular polysaccharide serotype 2 obtained above was sized mechanically using high-pressure homogenizer at 1000 bar, for 1 to 20 cycles. Sized polysaccharide preparation was concentrated again to 15 mg/mL on 30-kDa Ultra-Filter (UF) membrane. The retentate was passed through 0.22 μm filter and frozen below −20° C.

Sizing of Pneumococcal Capsular Polysaccharide from Serotypes 35B was Carried out Using Similar Procedure Described Above for Serotype 2.

e. Sizing of the Purified Pneumococcal Capsular Polysaccharides Serotype 15A

Purified pneumococcal capsular polysaccharides serotype 15A was sized mechanically using high-pressure homogenizer at 1500 bar, for 1 to 20 cycles. Sized polysaccharide pneumococcal serotype 15A preparation was concentrated again to 15 mg/mL on 30-kDa Ultra-Filter (UF) membrane. The retentate was passed through 0.22 μm filter and frozen below −20° C.

f. Sizing of the Purified Pneumococcal Capsular Polysaccharides Serotype 15C

Purified pneumococcal capsular polysaccharides serotype 15C was sized mechanically using high-pressure homogenizer at 1200 bar, for 1 to 20 cycles. Sized polysaccharide pneumococcal serotype 15A preparation was concentrated again to 15 mg/mL on 30-kDa Ultra-Filter (UF) membrane. The retentate was passed through 0.22 μm filter and frozen below −20° C.

NMR Structure Analyses of Pneumococcal Capsular Polysaccharides Serotype 2, 15A and 15C.

Figure 2:
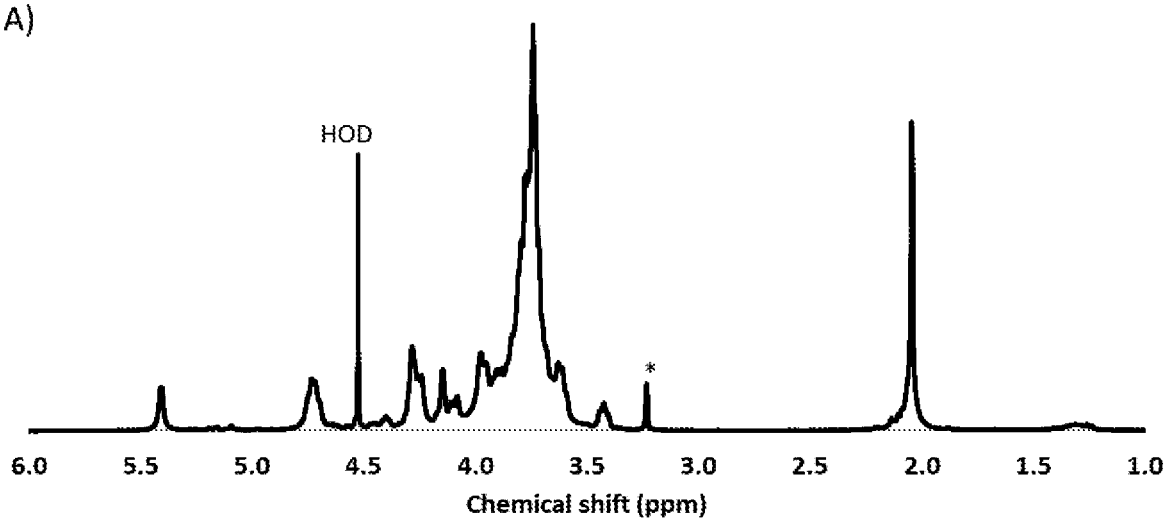
FIG. 2A: 400 MHz one dimensional (1D) $_1$H NMR spectrum of the capsular polysaccharide of Serotype 15A in D$_2$O at 50° C.
FIG. 2B: One dimensional (1D) $^1$H NMR identity region used for identification of serotype 15A.
Figure 2:
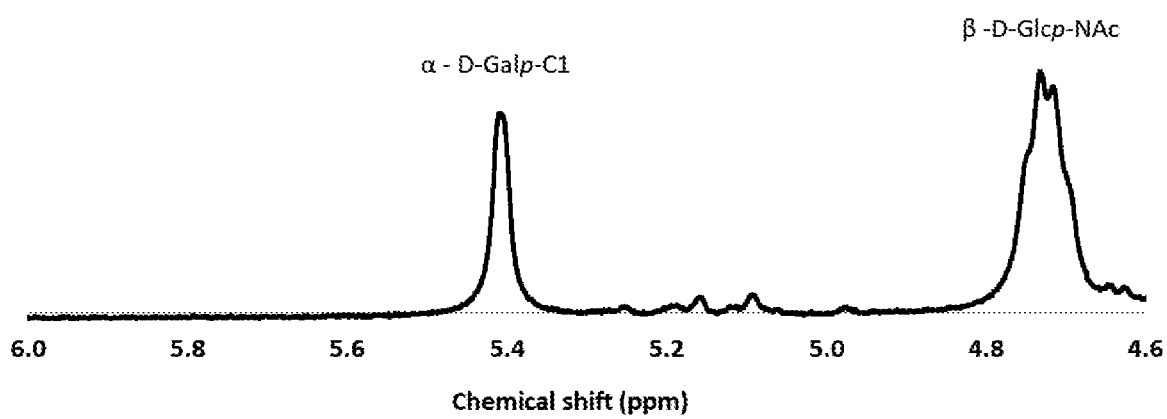
Figure 3:
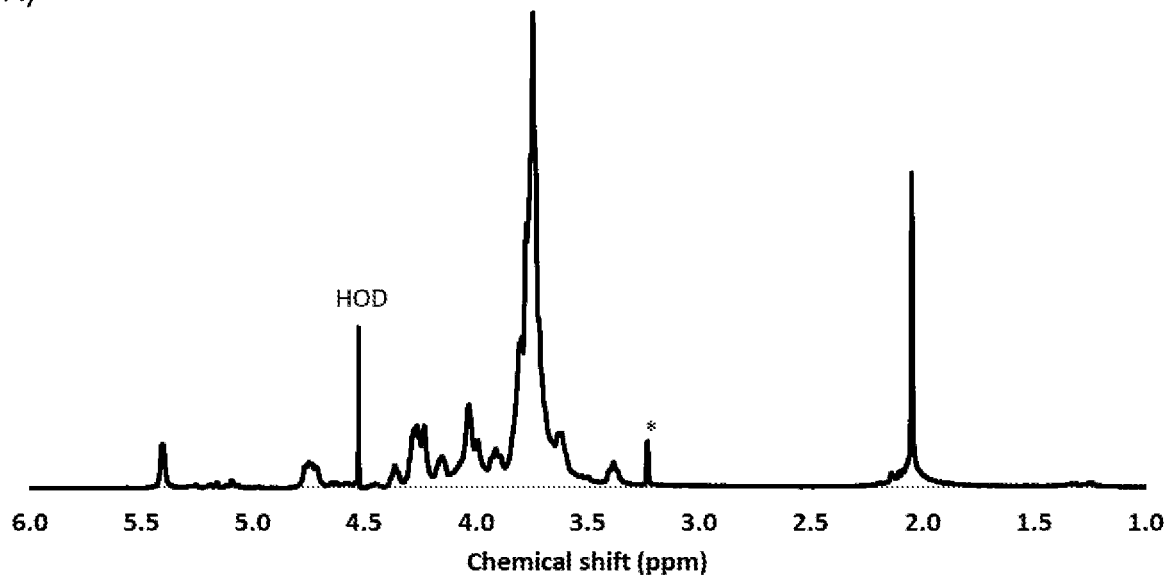
FIG. 3A: 400 MHz one dimensional (1D) $_1$H NMR spectrum of the capsular polysaccharide of Serotype 15C in D$_2$O at 50° C.
FIG. 3B: One dimensional (1D) $^1$H NMR identity region to be used for identification of serotype 15C.
Figure 3:
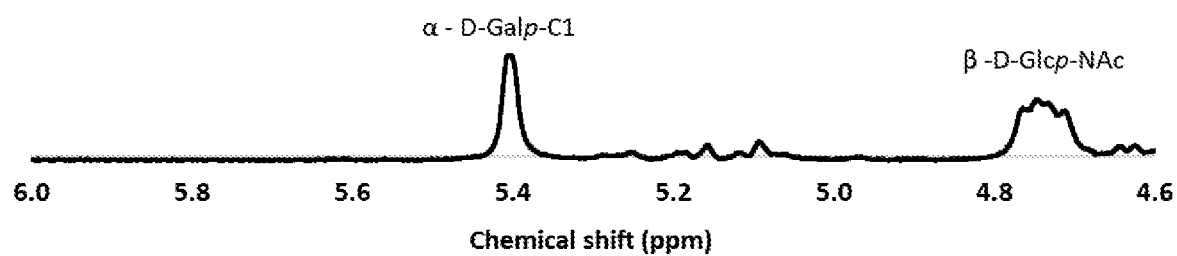

Confirmation of the polysaccharide identity for serotypes 2, 15A and 15C was done by NMR analysis. The analysis was performed based on the published methodology by Abeygunawardana et. al., Development and Validation of an NMR based Identity Assay for polysaccharides, *Analytical Biochemistry*, 279, 226-240 (2000). Based on the NMR data in FIGS. 1-3, the anomeric region of the NMR spectra confirms the polysaccharide identity and the peaks are identified for the sugars containing in respective polysaccharide serotypes 2, 15A and 15C.

NMR Structure Analyses of Pneumococcal Capsular Polysaccharides Serotype 35B.

Figure 4:
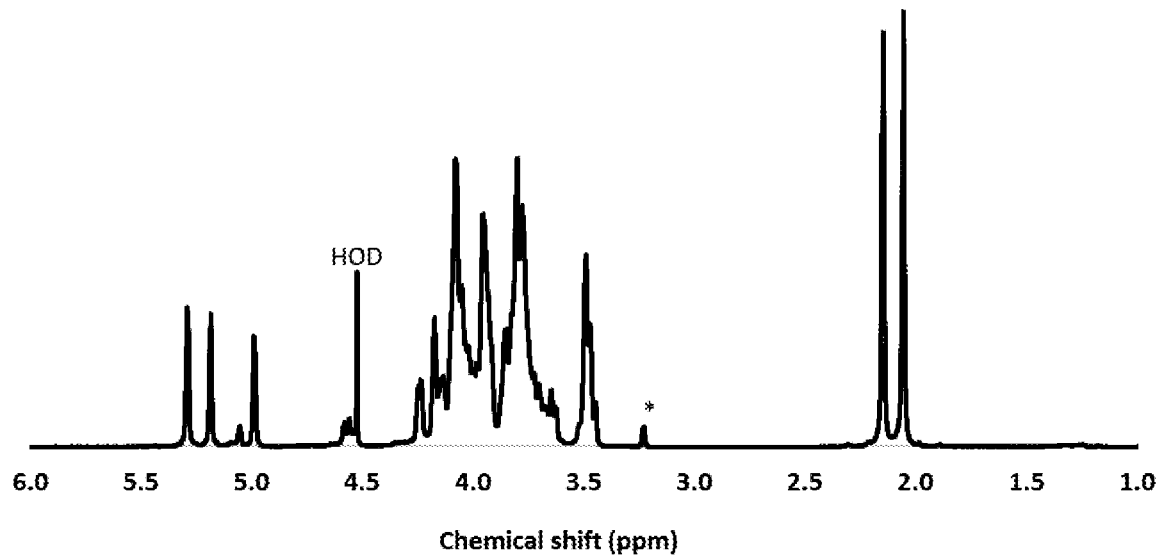
FIG. 4A: 400 MHz one dimensional (1D) $_1$H NMR spectrum of the capsular polysaccharide of Serotype 35B in D$_2$O at 50° C.
FIG. 4B: One dimensional (1D) $^1$H NMR identity region to be used for serotype identification of 35B.
Figure 4:
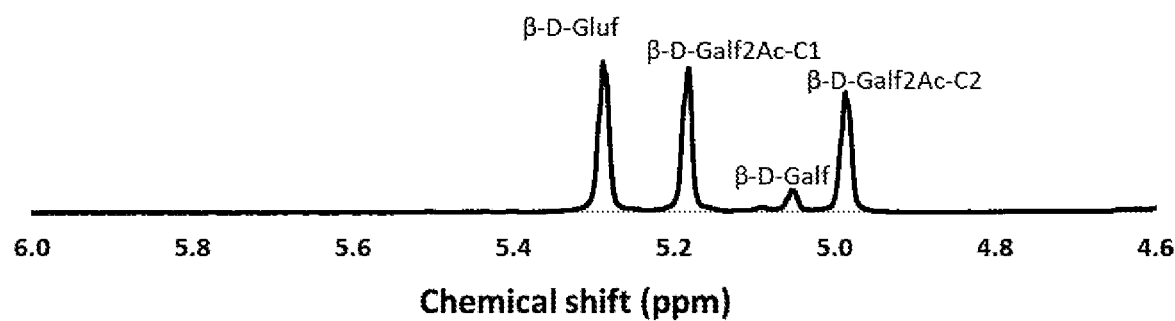

Confirmation of the polysaccharide identity for serotype 35B was done by NMR analysis. The analysis was performed based on the published methodology by Abeygunawardana et. al., Development and Validation of an NMR based Identity Assay for polysaccharides, *Analytical Biochemistry*, 279, 226-240 (2000). Based on the NMR data in FIG. 4. The $^1$H NMR spectra peak assignment of serotype 35B was done according to the published data by, L. M. Beynon., J. C. Richards., M. B. Perry., P. J. Kniskern, Characterization of the capsular antigen of *Streptococcus pneumoniae* serotype 35B, *Canadian Journal of Chemistry*, 73(1): 41-48 (1995).

The salient features of the purified and sized polysaccharides from pneumococcal serotypes 2, 15A, 15C and 35B prepared as described above, are mentioned in Table 1 below.

TABLE 1

| | | | | Post size | | | | |
|---|---|---|---|---|---|---|---|---|
| Serotype | Pre size Avg. Mol. Wt. (kDa) | Avg Mol Wt (kDa) | % of protein impurity | % of Nucleic acid impurity | % of CWPS | O-Acetyl (%) | Hexosamine (%) | Glycerol Content (%) |
| 2 | 545 | 261 | <1 | 0.1 | 0.82 | NA | NA | NA |
| 15A | 813 | 187 | <1 | 0.09 | 1.88 | <0.5 | 22.15 | 7.53 |
| 15C | 649 | 202 | <1 | 0.01 | 0.38 | <0.5 | 13 | 8.12 |
| 35B | 343 | 229 | <1 | 0.12 | 0.71 | 5.47 | 13 | N.A. |

Example 2

Preparation of Carrier Proteins a. Preparation of $CRM_{197}$ $CRM_{197}$ may be prepared by recombinant methods in accordance with the methods described in U.S. Pat. No. 5,614,382. Alternatively, $CRM_{197}$ is prepared recombinantly in accordance with the methods known in the literature or according to the method disclosed in PCT publication WO 2016/079755, WO 2017/081700 and WO 2018/193475. $CRM_{197}$ may be purified by ultrafiltration, ammonium sulphate precipitation, and ion-exchange chromatography, methods well known in the art.

b. Preparation of PsaA

The PsaA gene was PCR amplified from *Streptococcus pneumoniae* Serotype 4, without its hydrophobic leader peptide sequence. The gene sequence was verified and cloned into *Escherichia coli* using a vector constructed in-house (pBE66) for higher expression.

Glycerol stock culture encoding the PsaA gene was revived on a 20 mL LB Media containing 1 mL of Glycerol Stock in a 150 mL conical flask. The culture was incubated for about 6 hrs at 37° C. under 200 rpm to a final $OD_{600nm}$ of 3.5 OD. The revived culture was transferred to 1 L seed culture in a 5 L conical flask. The culture was grown for about 10 hrs at 37° C. under 200 rpm to a final OD 600 nm of 3. The seed culture was transferred aseptically to a 20 L fermenter containing the following media components, HyPeptone 6 g/L, Yeast extract 12/L, di Potassium Hydrogen ortho phosphate 13.5 g/L, ammonium phosphate di basic 4 g/L, Citric acid 1.7 g/L, $MgSO_4.7H_2O$ 1.2 g/L, Glucose 4 g/L, thiamine HCL 10 mg/L along with 1 mL/L trace elements (e.g., trace elements for 100 mL composition $FeCl_3$ 2.7 g, $ZnCl_2$ 0.2 g, $CoCl_2.6H_2O$ 0.2 g, $Na_2MoO_4.2H_2O$ 0.2 g, $CuSO_4$ $5H_2O$ 0.1 g, Boric Acid 0.05 g, $CaCl_2$ $2H_2O$ 0.1 g, Conc., HCL 10 mL). The initial fermentation started with $OD_{600}$ nm 0.2 OD. The pH was maintained at 7±0.2 throughout the fermentation with 20% ortho-phosphoric acid and 12.5% ammonium hydroxide. When the glucose level falls below 0.5 g/L the feed batch was initiated at a steady rate of 3-4 g/L/hr, the DO % was maintained >20% throughout the fermentation with oxygen enrichment. Cells were grown in the fermentor and the cell pellet was harvested by centrifugation. The cells were lysed using cell-disruption device (Panda). The lysate was centrifuged at 10000 g, the clarified supernatant was subject to purification.

PsaA purification was performed similarly to the procedure described in Larentis et. al, 2011 (Protein expression and Purification 78 (2011) 38). Purification was further optimized by using mixed mode chromatography (Ceramic Hydroxyapatite Type-II) after DEAE to achieve higher purity of PsaA.

Anion Exchange Chromatography: 30 mL of DEAE Sepharose (GE) resin was packed in XK16/20 column. The resin was washed with 5 column volumes of sterile distilled water followed by 10 column volumes of 20 mM Tris, 1 mM EDTA, pH 8.0 (Equilibration buffer). 30 mL of supernatant was diluted to 100 mL with equilibration buffer and loaded onto column and flow-through was collected. The column was washed with 5 volumes of equilibration buffer. PsaA was eluted with 12 volumes of linear gradient of (0-100% B). (Buffer A containing 20 mM Tris, 1 mM EDTA pH 8.0; Buffer B-20 mM Tris, 1 mM EDTA, 250 mM NaCl pH 8.0.) This was followed by washing the columns with 20 mM Tris, 1 mM EDTA, 1 M NaCl pH8.0.

Mixed Mode Chromatography: 25 ml of Ceramic Hydroxyapatite Type II (CHT-II) was packed in a column. The resin was washed with volumes of sterile distilled water followed by 10 volumes of 20 mM Tris pH 6.8. Elution fractions from DEAE resin that showed clear major visible band of approximately 37 KD good concentration of PsaA on SDS PAGE were pooled and loaded onto CHT-II resin. The flow-through was collected and the column was washed with 5 column volumes of equilibration buffer. Protein was eluted with 5 column volumes step gradients of (15% B, 20% B, 50% B and 100% B). Buffer A contains 20 mM Tris pH 6.8, while the Buffer B contains 250 mM Phosphate buffer pH 6.8.

All the elution fractions showing a clean band at the expected size of PsaA were pooled, concentrated by 10 kDa MWCO cassette and diafiltered against 20 mM Phosphate buffer pH 7.5. The purified protein was loaded on SDS-PAGE gel to assess purity.

Example 3

Conjugation of Pneumococcal Capsular Polysaccharides Serotype 2, 15A, 15C and 35B a. Conjugation of Pneumococcal Capsular Polysaccharides Serotype 2 with $CRM_{197}$ 1000 mg (200.0 mL of 5.0 mg/mL concentration) mechanically size reduced polysaccharide serotype 2 and 5.0 mL of CDAP (100 mg/mL in Acetonitrile (w/v)) was mixed in a glass bottle in the ratio of 1.0:0.5 (PS: CDAP) and stirred for 1 min. The pH of the polysaccharide solution was adjusted to 9.0 with 12.0 mL of 0.2M triethylamine and stirred for 1 min at room temperature (RT). 1000 mg of CRM (66.7 mL of 15.0 mg/mL concentration) was added slowly to the activated polysaccharide in a ratio of 1.0:1.0 (PnPs: CRM).

Figure 5:
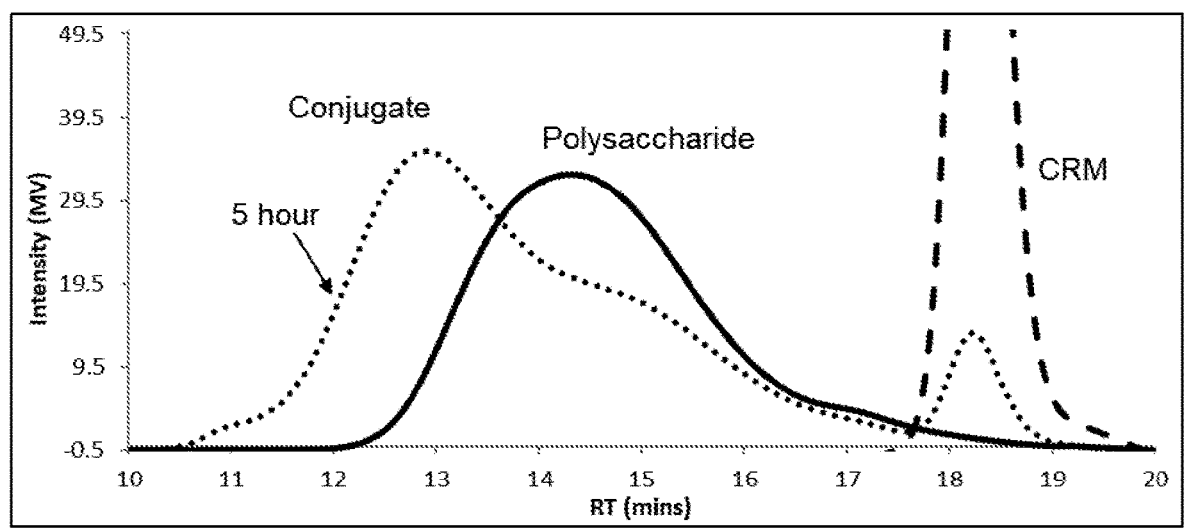
FIG. 5A: SEC-HPLC chromatogram illustrating conjugation reaction kinetics of serotype 2-CRM$_{197}$.
FIG. 5B: SEC-HPLC chromatogram illustrating conjugation reaction kinetics of serotype 2-PsaA.
Figure 5:
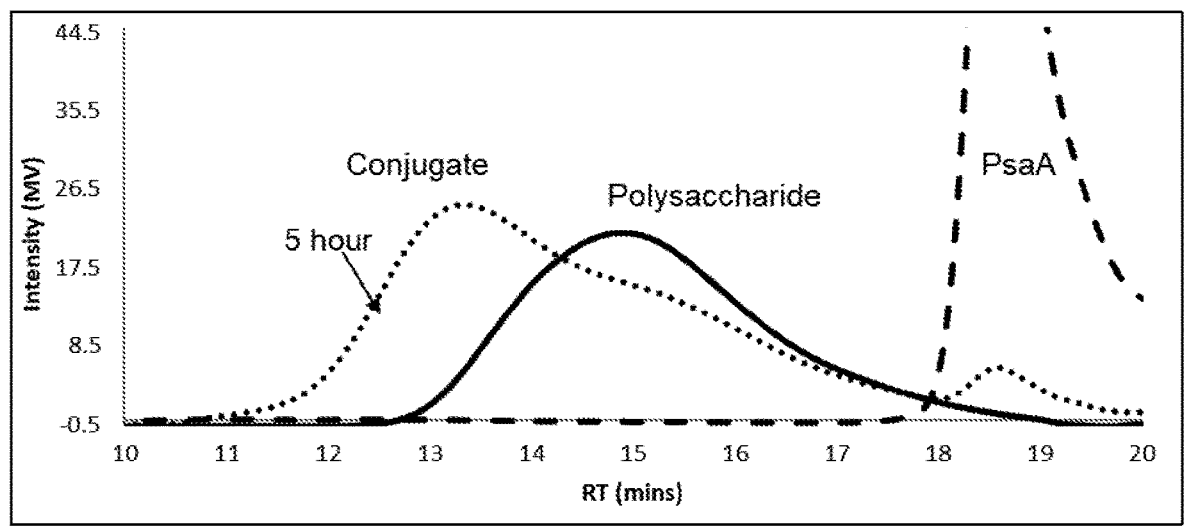

The pH of the reaction was adjusted to 9.0 with 2.8 mL of 0.2M triethylamine and the reaction was continued under stirring for 3-5 hours at room temperature followed by quenching of the reaction by adding an excess concentration of glycine (100 mM). The conjugation kinetics (FIG. 5A) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 8168 kDa.

b. Conjugation of Pneumococcal Capsular Polysaccharides Serotype 2 with PsaA 1000 mg (200.0 mL of 5.0 mg/mL concentration) of mechanically size reduced polysaccharide serotype 2 and 5.0 mL of CDAP (100 mg/mL in Acetonitrile (w/v)) was mixed in a glass bottle in the ratio of 1.0:0.5 (PS: CDAP) and stirred for 1 Min. The pH of the polysaccharide solution was adjusted to 9.0 with 16.0 mL of 0.2M triethylamine and stirred for 1 min at room temperature (RT). 800 mg of PsaA (53.33 mL of 15.0 mg/mL concentration) was added slowly to the activated polysaccharide in a ratio of 1.0:0.8 (PnPs: PsaA).

The pH of the reaction was adjusted to 9.0 with 3.5 mL of 0.2M triethylamine and the reaction was continued under stirring for 3-5 hours at room temperature followed by quenching of the reaction by adding an excess concentration of glycine (100 mM). The conjugation kinetics (FIG. 5B) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 6295 kDa.

c. Conjugation of Pneumococcal Capsular Polysaccharides Serotype 15A with $CRM_{197}$ 1000 mg (66.7 mL of 15.0 mg/mL concentration) mechanically size reduced polysaccharide serotype 15A and 10.0 mL of CDAP (100 mg/mL in Acetonitrile (w/v)) was mixed in a glass bottle in the ratio of 1.0:1.0 (PS: CDAP) and stirred for 1 min. The pH of the polysaccharide solution was adjusted to 9.0 with 18.0 mL of 0.2M triethylamine and stirred for 1 min at room temperature (RT). 1000 mg of $CRM_{197}$ (53.3 mL of 15.0 mg/mL concentration) was added slowly to the activated polysaccharide in a ratio of 1.0:0.8 (PnPs: CRM).

Figure 6:
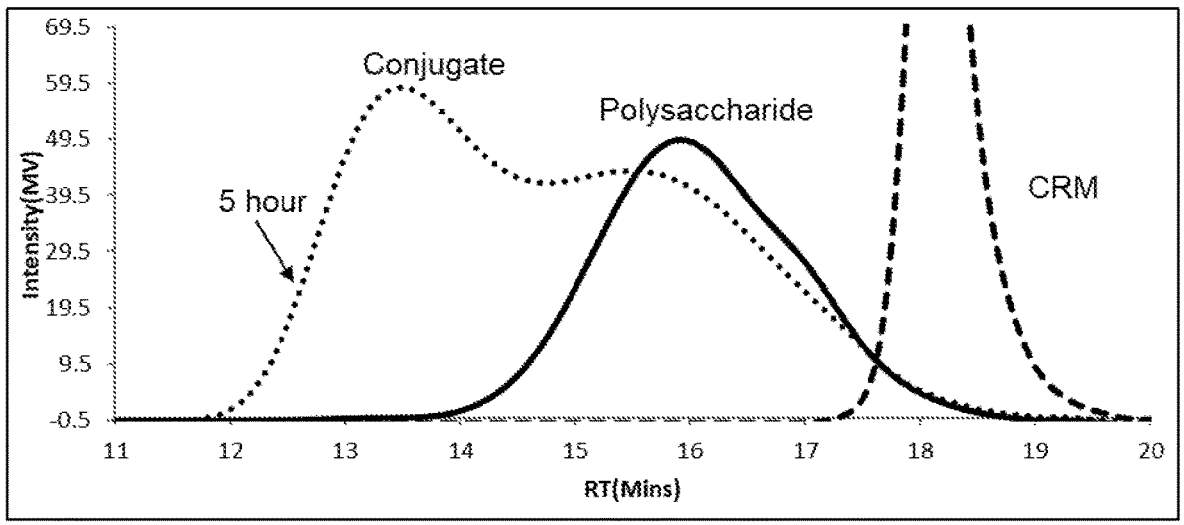
FIG. 6A: SEC-HPLC chromatogram illustrating conjugation reaction kinetics of (A) serotype 15A-CRM$_{197}$.
FIG. 6B: SEC-HPLC chromatogram illustrating conjugation reaction kinetics of serotype 15A-PsaA.
Figure 6:
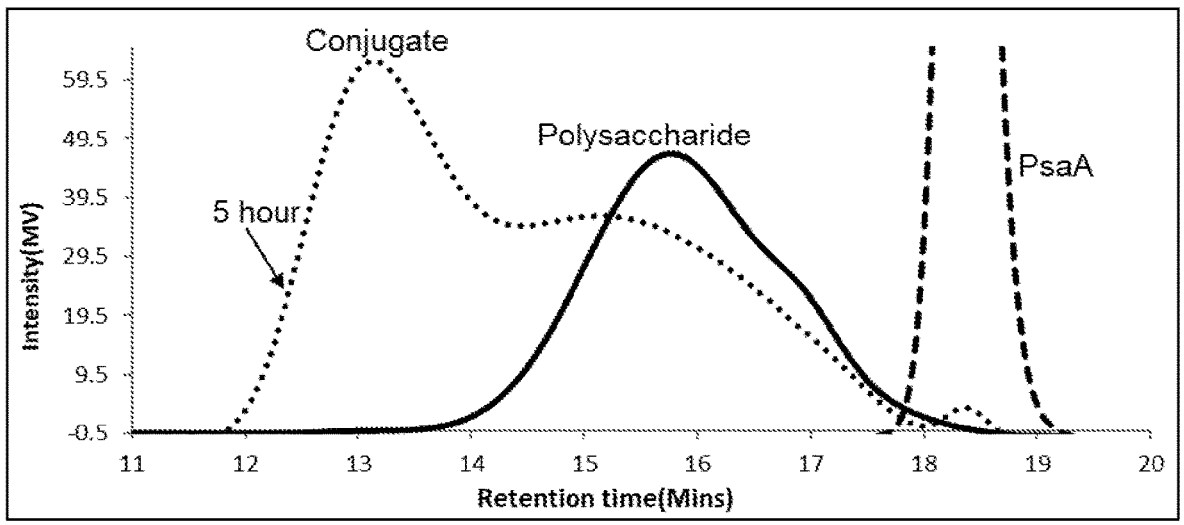

The pH of the reaction was adjusted to 9.0 with 1.0 mL of 0.2M triethylamine and the reaction was continued under stirring for 3-5 hours at room temperature followed by quenching of the reaction by adding an excess concentration of glycine (100 mM). The conjugation kinetics (FIG. 6A) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 4272 kDa.

d. Conjugation of Pneumococcal Capsular Polysaccharides Serotype 15A with PsaA 1000 mg (71.4 mL of 14.0 mg/mL concentration) mechanically size reduced polysaccharide serotype 15A and 10.0 mL of CDAP (100 mg/mL in Acetonitrile (w/v)) was mixed in a glass bottle in the ratio of 1.0:1.0 (PS: CDAP) and stirred for 1 Min. The pH of the polysaccharide solution was adjusted to 9.0 with 20.5 mL of 0.2M triethylamine and stirred for 1 min at room temperature (RT). 1000 mg of PsaA (66.6 mL of 15.0 mg/mL concentration) was added slowly to the activated polysaccharide in a ratio of 1.0:1.0 (PnPs: PsaA).

The pH of the reaction was adjusted to 9.0 with 0.9 mL of 0.2M triethylamine and the reaction was continued under stirring for 3-5 hours at room temperature followed by quenching of the reaction by adding an excess concentration of glycine (100 mM). The conjugation kinetics (FIG. 6B) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 9776 kDa.

e. Conjugation of Pneumococcal Capsular Polysaccharides Serotype 15C with $CRM_{197}$ 1000 mg (100.0 mL of 10.0 mg/mL concentration) of mechanically size reduced polysaccharide serotype 15C and 15.0 mL of CDAP (100 mg/mL in Acetonitrile (w/v)) was mixed in a glass bottle in the ratio of 1.0:1.5 (PS: CDAP) and stirred for 1 Min. The pH of the polysaccharide solution was adjusted to 9.0 with 24.0 mL of 0.2M triethylamine and stirred for 1 min at room temperature (RT). 1000 mg of $CRM_{197}$ (66.6 mL of 15.0 mg/mL concentration) was added slowly to the activated polysaccharide in a ratio of 1.0:1.0 (PnPs: CRM).

Figure 7:
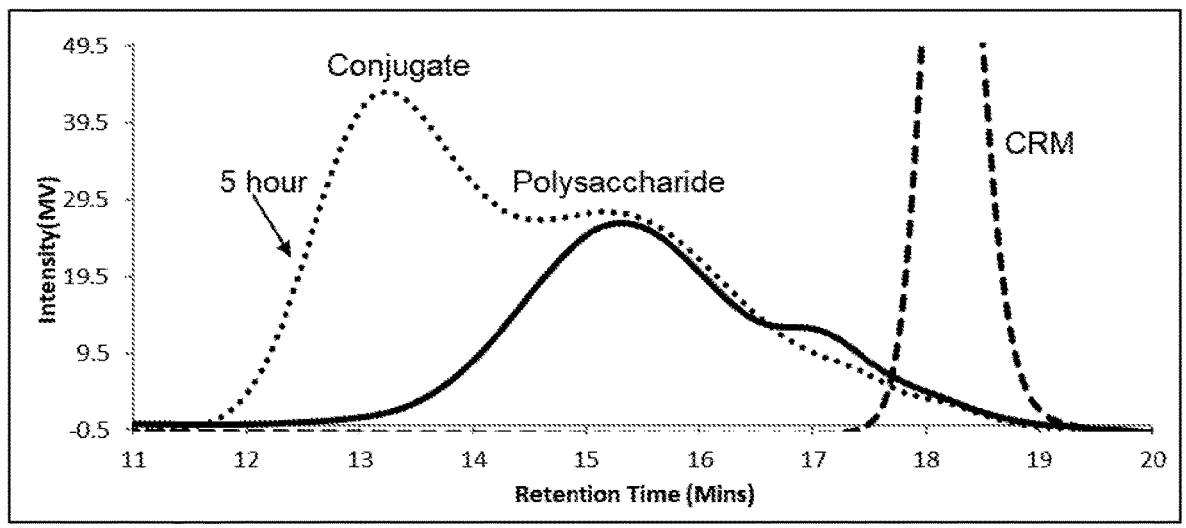
FIG. 7A: SEC-HPLC chromatogram illustrating conjugation reaction kinetics of (A) serotype 15C-CRM$_{197}$.
FIG. 7B: SEC-HPLC chromatogram illustrating conjugation reaction kinetics of serotype 15C-PsaA.
Figure 7:
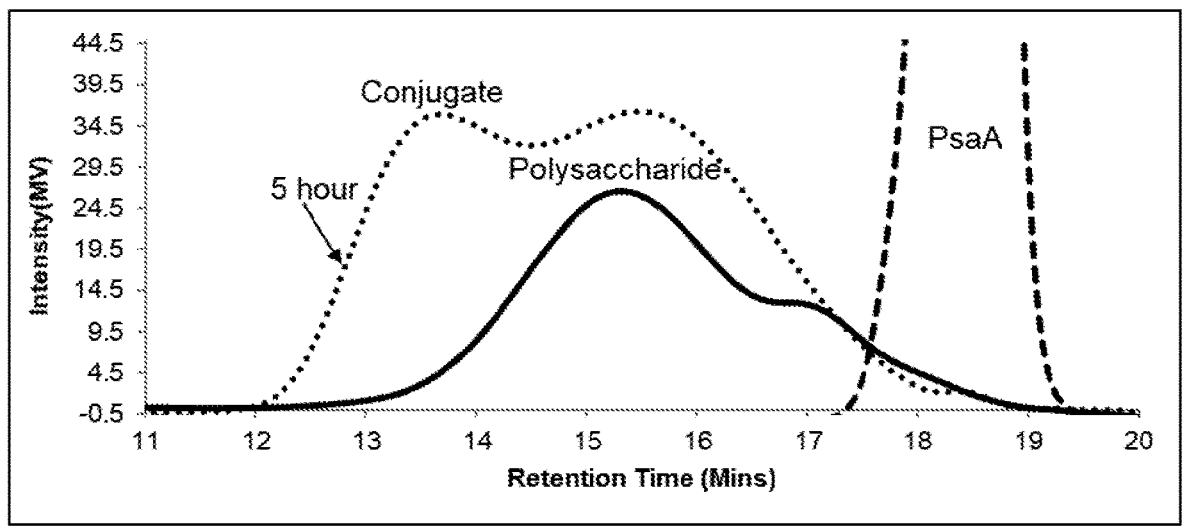

The pH of the reaction was adjusted to 9.0 with 2.8 mL of 0.2M triethylamine and the reaction was continued under stirring for 3-5 hours at room temperature followed by quenching of the reaction by adding excess concentration of glycine (100 mM). The conjugation kinetics (FIG. 7A) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 10490 kDa.

f. Conjugation of Pneumococcal Capsular Polysaccharides Serotype 15C with PsaA 1000 mg (100.0 mL of 10.0 mg/mL concentration) of mechanically size reduced polysaccharide serotype 15C and 15.0 mL of CDAP (100 mg/mL in Acetonitrile (w/v)) was mixed in a glass bottle in the ratio of 1.0:1.5 (PS: CDAP) and stirred for 1 Min. The pH of the polysaccharide solution was adjusted to 9.0 with 24.0 mL of 0.2M triethylamine and stirred for 1 min at room temperature (RT). 1000 mg of PsaA (66.6 mL of 15.0 mg/mL concentration) was added slowly to the activated polysaccharide in a ratio of 1.0:1.0 (PnPs: PsaA).

The pH of the reaction was adjusted to 9.0 with 2.8 mL of 0.2 M triethylamine and the reaction was continued under stirring for 3-5 hours at room temperature followed by quenching of the reaction by adding an excess concentration of glycine (100 mM). The conjugation kinetics (FIG. 7B) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 8719 kDa.

g. Conjugation of Pneumococcal Capsular Polysaccharides Serotype 35B with $CRM_{197}$ 1000 mg (100.0 mL of 10.0 mg/mL concentration) mechanically size reduced polysaccharide serotype 35B and 5.0 mL of CDAP (100 mg/mL in Acetonitrile (w/v)) was mixed in a glass bottle in the ratio of 1.0:0.5 (PS: CDAP) and stirred for 1 min. The pH of the polysaccharide solution was adjusted to 9.0 with 5.0 mL of 0.2M triethylamine and stirred for 1 min at room temperature (RT). 1000 mg of $CRM_{197}$ (66.7 mL of 15.0 mg/mL concentration) was added slowly to the activated polysaccharide in a ratio of 1.0:1.0 (PnPs: CRM).

Figure 8:
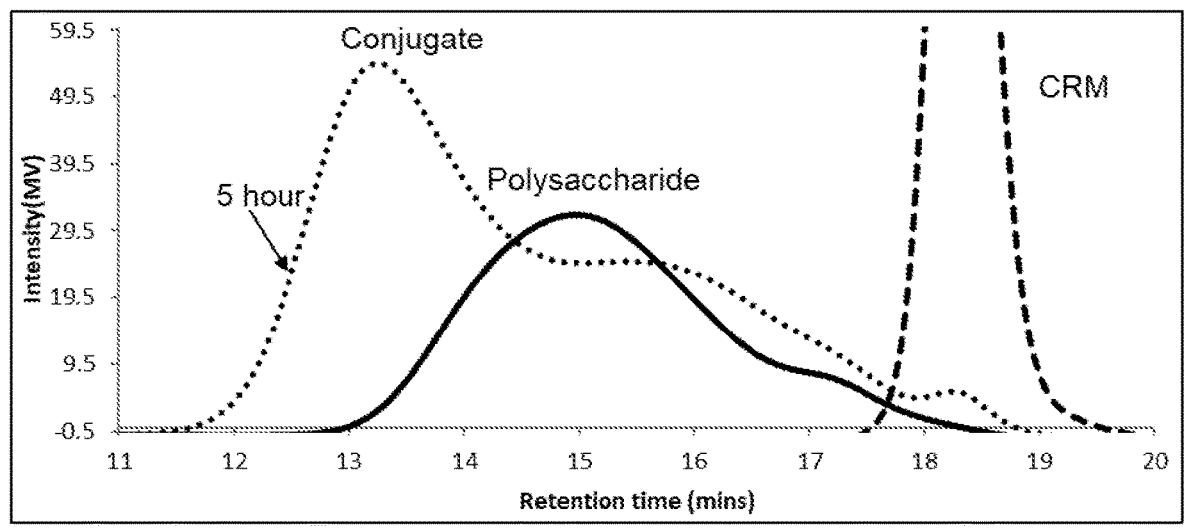
FIG. 8A: SEC-HPLC chromatogram illustrating conjugation reaction kinetics of (A) serotype 35B-CRM$_{197}$.
FIG. 8B: SEC-HPLC chromatogram illustrating conjugation reaction kinetics of serotype 35B-PsaA.
Figure 8:
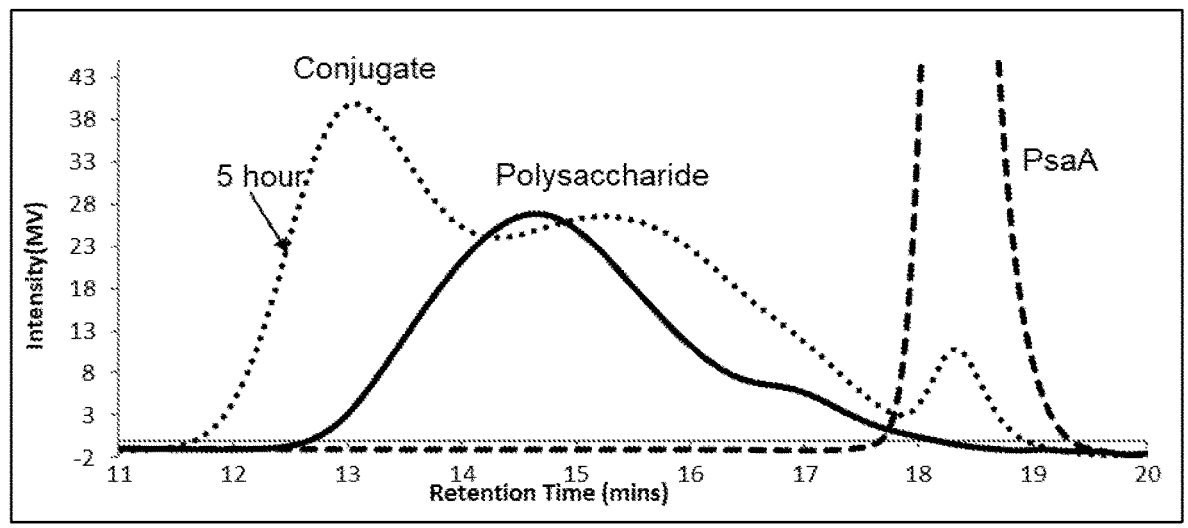

The pH of the reaction was adjusted to 9.0 with 1.6 mL of 0.2M triethylamine and the reaction was continued under stirring for 3-5 hours at room temperature followed by quenching of the reaction by adding an excess concentration of glycine (100 mM). The conjugation kinetics (FIG. 8A) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analysed by SEC-MALLS, anthrone method and fractions containing conjugates were pooled and sterile filtered with 0.2 pm filters. The average molecular weight of the conjugate obtained was 8572 kDa h. Conjugation of Pneumococcal Capsular Polysaccharides Serotype 35B with PsaA 1000 mg (142.8 mL of 7.0 mg/mL concentration) mechanically size reduced polysaccharide serotype 35B and 6.0 mL of CDAP (100 mg/mL in Acetonitrile (w/v)) was mixed in a glass bottle in the ratio of 1.0:0.6 (PS: CDAP) and stirred for 1 min. The pH of the polysaccharide solution was adjusted to 9.0 with 7.0 mL of 0.2M triethylamine and stirred for 1 min at room temperature (RT). 1000 mg of PsaA (66.6 mL of 15.0 mg/mL concentration) was added slowly to the activated polysaccharide in a ratio of 1.0:1.0 (PnPs: PsaA).

The pH of the reaction was adjusted to 9.0 with 2.2 mL of 0.2M triethylamine and the reaction was continued under stirring for 3-5 hours at room temperature followed by quenching of the reaction by adding excess concentration of glycine (100 mM). The conjugation kinetics (FIG. 8B) of reactions were monitored using SEC-HPLC at each hour of the reaction.

The reaction mixture was diafiltered and concentrated using 100 kDa MWCO TFF membrane. The concentrate was purified by size-exclusion chromatography. The fractions were analyzed by SEC-MALLS, anthrone method and fractions containing conjugates were pooled and sterile filtered with 0.2 pm filters. The average molecular weight of the conjugate obtained was 6944 kDa.

Example 4

Formulation of Pneumococcal Capsular Polysaccharide-protein Conjugate Vaccine

A multivalent conjugate vaccine was formulated as 0.5 mL dose containing 2.2 μg of each pneumococcal polysaccharide from serotypes 2, 15A, 15C, and 35B conjugated to ~8-10 μg of $CRM_{197}$ protein prepared in example 3. All the conjugates were adsorbed on to aluminum phosphate gel equivalent to 0.5 mg $Al^{3+}$ per dose of 0.5 mL. The 0.9% W/V saline was used as diluent and vehicle for the formulation and the final formulation pH was adjusted to pH 6 using 1N hydrochloric acid. For effective adsorption post adjusting the pH, the formulation was mixed for 2 hours under constant stirring. After 2 hours of blending, the formulated blend was aseptically filled at 0.58 mL fill volume per vial into the 3 mL sterile nonsiliconized vials, closed with sterile 13 mm rubber stoppers and sealed with 13 mm sterile pink colored flip off aluminium seals, followed by optical inspection and labelling of filled vials. From the lot, some vials were randomly picked up and analyzed for the appearance, pH, Osmolality, total poly and protein content (μg/SHD), % Adsorption, aluminium content (mg/SHD).

Example 5

Formulation of Pneumococcal Capsular Polysaccharide-protein Conjugate Vaccine

A multivalent conjugate vaccine was formulated as 0.5 mL dose containing 2.2 μg of each pneumococcal polysaccharide from serotypes 2, 15A, 15C, and 35B conjugated to ~8-10 μg of PsaA carrier protein prepared in example 3. All the conjugates were adsorbed on to aluminium. All the conjugates were adsorbed on to aluminium phosphate gel equivalent to 0.5 mg $Al^{3+}$ per dose of 0.5 mL. The 0.9% W/V saline was used as diluent and vehicle for the formulation and the final formulation pH was adjusted to pH 6 using 1N hydrochloric acid. For effective adsorption post adjusting the pH, the formulation was mixed for 2 hours under constant stirring. After 2 hours of blending, the formulated blend was aseptically filled at 0.58 mL fill volume per vial into the 3 mL sterile nonsiliconized vials, closed with sterile 13 mm rubber stoppers and sealed with 13 mm sterile pink colored flip off aluminium seals, followed by optical inspection and labelling of filled vials. From the lot, some vials were randomly picked up and analyzed for the appearance, pH, Osmolality, total poly and protein content (μg/SHD), % Adsorption, aluminium content (mg/SHD).

Example 5

Formulation of Pneumococcal Capsular Polysaccharide-protein Conjugate Vaccine

A 24 valent conjugated vaccine was formulated as 0.5 mL dose containing 2.2 μg of each pneumococcal polysaccharide from serotypes 1, 4, 5, 6B, 7F, 9V, 14, 18C, 19A, 19F, 22F, 23F and 33F except 4.4 μg of 6B conjugated to 25 to 40 μg $CRM_{197}$ and 2.2 μg of each pneumococcal polysaccharide from serotypes 3, 6A, 8, 10A, 11A, 12F, 15A, 23A, 23B, 24F and 35B were conjugated to 25 to 40 μg of PsaA. All the conjugates were adsorbed on to aluminum phosphate gel equivalent to 0.5 mg $Al^{3+}$ per dose of 0.5 mL The 0.9% WN saline was used as diluent and vehicle for the formulation and the final formulation pH was adjusted to pH 6 using 1N hydrochloric acid. For effective adsorption post adjusting the pH, the formulation was mixed for 2 hours under constant stirring. After 2 hours of blending, the formulated blend was aseptically filled at 0.58 mL fill volume per vial into the 3 mL sterile non-siliconized vials, closed with sterile 13 mm rubber stoppers and sealed with 13 mm sterile pink colored flip off aluminum seals, followed by optical inspection and labelling of filled vials. From the lot, some vials randomly picked were sent for analyzing the appearance, pH, Osmolality, total poly and protein content (μg/SHD), % Adsorption, aluminum content (mg/SHD).

Example 6

Immunization of Rabbits with 0.5 mL Dose a. Immunization and ELISA

Healthy rabbits 1.5 to 2 kg each were bred and reared in a contained facility. Rabbits were immunized with a single 0.5 mL dose of multivalent PCV as described in Examples 4 and 5. Each group, consisting of 7 rabbits, were immunized with formulation on days 1, 15 and 29. Blood samples were collected on days 0 (pre-immune), 15 (test bleed) and 36 (final bleed). Rabbit sera collected on day 0 (PD1) and Day 40 (PD3) were analyzed for serotype specific immune response using ELISA. The ELISA was performed as per the WHO suggested protocol. The ELISA was performed as per the WHO suggested protocol. Briefly, Maxisorp™ ELISA plates were coated with PnCPS of given serotype. The ELISA was performed as per the WHO suggested protocol. Briefly, Maxisorp™ ELISA plates were coated with PnCPS of given serotype (1 μg/50 μL/well using PBS; sterile endotoxin free, with 0.02% sodium azide). Plates were placed in a box with moistened paper towels for humidification and incubated at 37° C.±2° C. for 5 hrs, the plates were then stored at 5° C.±3° C. until use.

The test sera were pre-adsorbed to CWPS Mlti™ to eliminate background reactivity originating from cell-wall polysaccharide. To achieve this 2 μL of test and positive control serum was diluted using 998 μL pre-adsorption solution (1 mL-1 μL CWPS Multi™ in 999 μL of 10% SuperBlock™ in PBST) to get final dilution of 1:500. The diluted samples were incubated at room temperature (25° C.±5° C.) for 1 hr with continuous shaking. The unbound PnCPS were removed by flicking the plate and the free sites in the wells were blocked by adding 200 μL of blocker (20% SuperBlock™ in PBS). The plates were incubated at room temperature (25° C.±5° C.) for 1 hr without shaking.

b. Test Samples and Controls Addition

50 μL diluent (10% SuperBlock™ in PBST) was added to all wells except A1 to A12. Following this 100 μL/well preadsorbed test sera samples were added to A1 to A10, control sera samples were added to A11 and A12. Two-fold serial dilution of test samples was performed by transferring 50 μL from $1^{st}$ to $2^{nd}$ and so on, i.e., from A1-A10 to H1-H10. Similarly, serial dilution of control samples (007SP) from A11 and 12 to E11 and E12 were performed. F11 and F12 to H11 and H12 without dilution were set up as blank. The plates were incubated at room temperature (25° C.±5° C.) for 2 hrs without shaking. Following the incubation step the contents were discarded and the plates were washed thrice with PBST (~250 μL/well) manually or with plate washer.

c. Primary Antibody Addition

50 μL/well recombinant protein NG peroxidase (diluted 1:20000 using 10% SuperBlock™ in PBST) was added to all wells and the plates were incubated for 1 hr at room temperature (25° C.±5° C.) without shaking. Following this, the plates were washed thrice with PBST (250 μL/well) manually or with plate washer.

d. Development and Reading

Chromogenic reaction was developed by adding 50 μL/well TMB substrate and incubated for 15 mins at room temperature (25° C.±5° C.) without shaking. The reaction was stopped by adding 50 μL/well 1.25M Sulphuric acid. The OD at 450 nm was measured.

e. Titer Estimation

Antibody titer in the immunized animals was assigned as inverse of dilution factor. The highest dilution showing $OD_{450nm}$ as twice the pre-immune titer (approximately 0.2) was reported as titer. The titer of serum antibody to each serotype was plotted and compared with different treatment groups.

f. Immune Response in Rabbits

Rabbits were immunized with the formulation described in Example 5. The study design consisted of two groups of 7 rabbits each. Animals were immunized with three doses of the formulated vaccines.

Serum from the immunized rabbits were collected at specified interval. Serotype specific IgG titer levels were estimated in an ELISA, which is adapted from a WHO recommended ELISA to assess serum antibody titers in human serum. Antibody titers were estimated as—maximum dilution of the serum that gave $OD_{450nm}$ value above the cut-off limit. The IgG titer value of pre-vaccinated animal was used to calculate Geometric Mean Fold Rise (GMFR) in serum IgG titer. After administration of the 24 valent PCV formulation described above, the animals were found to have antibodies against each serotype of polysaccharide of the conjugate in the vaccine, and therefore, these vaccines are immunogenic.

Figure 9:
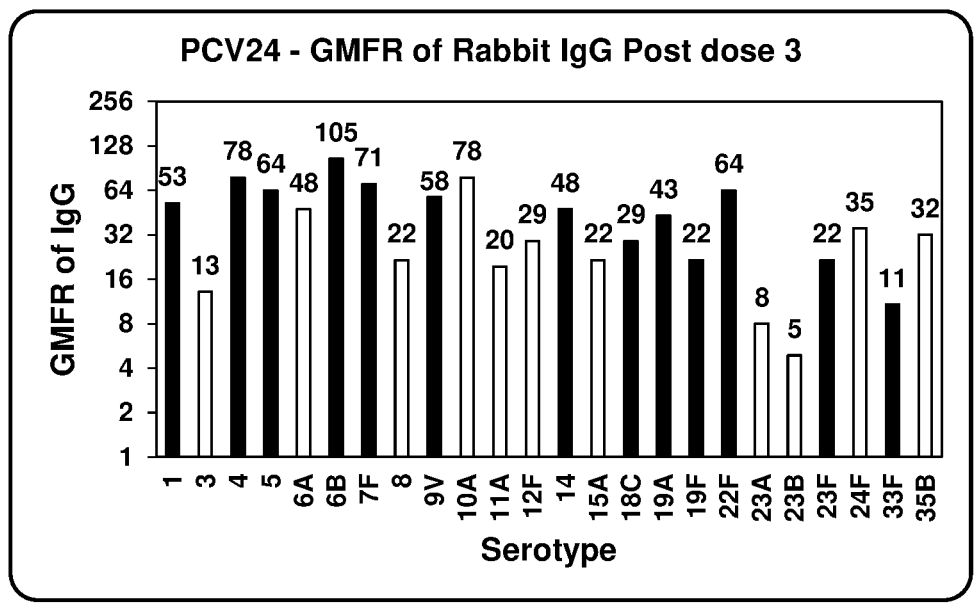
FIG. 9: Serum antibody titers in rabbits immunized with PCV formulation.

As shown in (FIG. 9), the titre is estimated as maximum serum dilution that produced ELISA $OD_{450nm}$ above the cut-off value ($2 \times OD_{450nm}$ observed in pre-immune sera; OD value of about 0.1). Geometric Mean Fold Rise (GMFR) for each serotype was plotted. The sera obtained after 3 doses of immunization (Post dose 3) was used to assess the immunogenicity. Solid black bars indicate pneumococcal polysaccharides conjugated to CRM197, while open while bars indicate pneumococcal polysaccharides conjugated to PsaA.

From the foregoing, it will be appreciated that specific embodiments of the invention have been described herein for purposes of illustration, but that various modifications may be made without deviating from the scope of the invention.

We claim:

1. A pneumococcal conjugate vaccine comprising a 1-cyano-4-dimethylaminopyridine tetrafluoroborate (CDAP)-activated purified capsular polysaccharide from serotype 15A having an average molecular weight between 100 kDa and 500 kDa conjugated to PsaA, wherein the composition comprises a (w/w) percent ratio of protein to polysaccharide (protein/PS) of 0.7 to 1.2.

2. The pneumococcal conjugate vaccine of claim 1, wherein the conjugate has an average molecular weight ranging between 500 kDa to 5000 kDa; 1,000 kDa to 10,000 kDa; 1,500 kDa to 15,000 kDa; 2,000 kDa to 20,000 kDa; 2,500 kDa to 25,000 kDa; or 3,000 kDa to 30,000 kDa.

3. An immunogenic composition comprising at least one glycoconjugate comprising a 1-cyano-4-dimethylaminopyridine tetrafluoroborate (CDAP)-activated purified capsular polysaccharide from serotype 15A having an average molecular weight between 100 kDa and 500 kDa conjugated to PsaA, wherein the glycoconjugate comprises a (w/w) percent ratio of protein to polysaccharide (protein/PS) of 0.7 to 1.2, and wherein the glycoconjugate has an average molecular weight ranging between 500 kDa to 30,000 kDa.

4. The immunogenic composition of claim 3, further comprising at least one glycoconjugate from *Streptococcus pneumoniae* serotypes 1, 2, 3, 4, 5, 6A, 6B, 7F, 8, 9V, 10A, 11A, 14, 15B, 15C, 16F, 18C, 19A, 19F, 22F, 23A, 23B, 23F, 24F, 31, 33F, and/or 35B conjugated to PsaA or CRM197.

5. The immunogenic composition of claim 4, wherein the composition is an 8, 9, 10, 11, 12, 13, 14, 15, 16, 17, 18, 19, 20, 22, 24, 25 or more valent pneumococcal conjugate composition.

6. The immunogenic composition of claim 5, wherein the composition is a 24 valent pneumococcal conjugate composition comprising the purified capsular polysaccharide from serotype 15A and polysaccharides from at least 2 pneumococcal serotypes selected from 2, 15C, and 35B and additional serotypes selected from 1, 3, 4, 5, 6A, 6B, 7F, 8, 9V, 10A, 11A, 14, 18C, 19A, 19F, 20A, 20B, 22F, 23F, 24F, and 33F, wherein the purified capsular polysaccharide from serotype 15A is conjugated to PsaA and each of the remaining polysaccharides is conjugated to PsaA or CRM197.

7. The immunogenic composition of claim 5, wherein the composition is a 24 valent pneumococcal conjugate composition comprising the purified capsular polysaccharide from serotype 15A and polysaccharides from at least 1 pneumococcal serotypes selected from 2, 15C, and 35B and additional serotype selected from 1, 3, 4, 5, 6A, 6B, 7F, 8, 9V, 10A, 11A, 12F, 14, 18C, 19A, 19F, 22F, 23A, 23B, 23F, 24F, and 33F, wherein the purified capsular polysaccharide from serotype 15A is conjugated to PsaA and each of the remaining polysaccharides is conjugated to PsaA or CRM197.

8. The immunogenic composition of claim 5, wherein the composition is a multivalent pneumococcal conjugate composition comprising the purified capsular polysaccharide from serotype 15A and polysaccharides from at least 2 pneumococcal serotypes selected from 2, 15C, and 35B and one or more additional serotypes selected from 1, 3, 4, 5, 6A, 6B, 7F, 8, 9V, 10A, 11A, 12F, 14, 18C, 19A, 19F, 20A, 20B, 22F, 23A, 23B, 23F, 24F, and 33F, wherein the purified capsular polysaccharide from serotype 15A is conjugated to PsaA and each of the remaining polysaccharides is conjugated to PsaA or CRM197.

9. The immunogenic composition of claim 5, wherein the composition is a 17 valent pneumococcal conjugate composition comprising polysaccharides from serotypes selected from 1, 2, 3, 4, 5, 6A, 6B, 7F, 9V, 14, 15A, 15C, 18C, 19A, 19F, 23F, and 35B, wherein the purified capsular polysaccharide from serotype 15A is conjugated to PsaA and each of the remaining polysaccharides is conjugated to PsaA or CRM197.

10. A method of treating a disease mediated by *Streptococcus pneumoniae* in a subject in need thereof, comprising administering an effective dose of the immunogenic composition of any one of claims 3-9 to the subject.

11. The pneumococcal conjugate vaccine of claim 1, wherein the purified capsular polysaccharide from serotype 15A is activated with CDAP prior to being conjugated to PsaA.

12. The immunogenic composition of claim 3, wherein the purified capsular polysaccharide from serotype 15A is activated with CDAP prior to being conjugated to PsaA.

\* \* \* \* \*